(12) United States Patent
Abbott et al.

(10) Patent No.: US 6,797,463 B2
(45) Date of Patent: Sep. 28, 2004

(54) METHOD AND APPARATUS FOR DETECTION OF MICROSCOPIC PATHOGENS

(75) Inventors: Nicholas L. Abbott, Madison, WI (US); Justin J. Skaife, Lafayette, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/784,232

(22) Filed: Feb. 15, 2001

(65) Prior Publication Data

US 2002/0028451 A1 Mar. 7, 2002

Related U.S. Application Data

(60) Provisional application No. 60/182,941, filed on Feb. 16, 2000.

(51) Int. Cl.⁷ .................. C12Q 1/70; G01N 33/53; G01N 21/47
(52) U.S. Cl. .............. 435/5; 435/4; 435/7.2; 435/287.1; 435/287.8; 435/288.7; 436/518; 436/807; 422/82.05
(58) Field of Search ............. 422/58, 102, 82.05; 435/4, 7.2, 287.1, 5, 287.8, 288.7; 436/518, 807; 204/403

(56) References Cited

U.S. PATENT DOCUMENTS

| | | | | |
|---|---|---|---|---|
| 4,597,942 A | * | 7/1986 | Meathrel ............... | 210/635 |
| 4,628,037 A | * | 12/1986 | Chagnon et al. ........ | 422/58 |
| 5,712,103 A | * | 1/1998 | Leavitt et al. ......... | 422/56 |
| 6,171,802 B1 | * | 1/2001 | Woolverton et al. ..... | 422/55 |
| 6,277,489 B1 | * | 8/2001 | Abbott et al. ......... | 436/518 |
| 6,284,197 B1 | * | 9/2001 | Abbott et al. ......... | 435/7.1 |

FOREIGN PATENT DOCUMENTS

| | | |
|---|---|---|
| DE | 3617710 A1 | 12/1986 |
| EP | 0 345 462 A2 | 12/1989 |
| EP | WO 92/08978 | 5/1992 |
| EP | WO 99/63329 | 12/1999 |
| EP | WO 99/64862 | 12/1999 |
| JP | 02311822 A2 | 12/1990 |
| JP | 02311824 A2 | 12/1990 |
| JP | 03010222 A2 | 1/1991 |

(List continued on next page.)

OTHER PUBLICATIONS

Alberti et al., Analysis of Complement C3 Deposition and degradation on Klebsiella pneumoniae, 1996, Infection and Immunity, 64(11):4726–4732.*

Encarta Dictionary, Oct. 16, 2002, http://encarta.msn.com/.*

Dr. Graham Dark, The On–line Medical Dictionary, Oct. 16, 2002, http/cancerweb.ncl.ac.uk/omd/index.html.*

Starkey, C.A. et al. "Evaluation of the Recombigen HIV–1 Latex Agglutionation Test", J. Clin. Microbiol., vol. 28, No. 4, Apr. 1990, pp. 819–822 published by the American Society for Microbiology.

(List continued on next page.)

Primary Examiner—Padmashri Ponnaluri
Assistant Examiner—My Chau T Tran
(74) Attorney, Agent, or Firm—Foley & Lardner LLP

(57) ABSTRACT

Detection apparatus for use in the detection of the presence of a selected pathogen in a sample are disclosed. Such apparatus include: a substrate with a detection region on a surface thereof, the detection region having microstructures including grooves formed therein that will align liquid crystal material in contact therewith, the width and depth of the grooves being in the range of 10 μm or less; a blocking layer on the surface of the detection region of the substrate that does not disrupt the alignment of liquid crystal material in contact therewith, the blocking layer blocking nonspecific adsorption of pathogens to the surface; and a binding agent on the surface of the detection region of the substrate, the binding agent specifically binding the selected pathogen.

15 Claims, 12 Drawing Sheets

FOREIGN PATENT DOCUMENTS

| | | |
|---|---|---|
| JP | 03039932 A2 | 2/1991 |
| JP | 04057024 A2 | 2/1992 |
| JP | 04057025 A2 | 2/1992 |
| JP | 04284423 A2 | 10/1992 |
| JP | 05134257 A2 | 5/1993 |
| JP | 05134258 A2 | 5/1993 |
| JP | 06175136 A2 | 6/1994 |
| JP | 06194513 A2 | 7/1994 |
| JP | 06194662 A2 | 7/1994 |

OTHER PUBLICATIONS

Häussling, L. et al, "Biotin–Functionalized Self–Assembled Monolayers on Gold: Surface Plasmon Optical Studies of Specific Recognition Reactions", Langmuir, vol. 7, No. 9, Sep. 1991, pp. 1837–1840, published by the American Chemical Society (Washington, D.C.).

Schmitt, F.–J. et al., "Surface Plasmon Studies of Specific Recognition Reactions at Self–Assembled Monolayers on Gold", Thin Solid Films, vol. 210/211, (1992), pp. 815–817, published by Elsevier Sequoia.

Charych, D.H. et al. "Direct Colorimetric Detection of a Receptor–Ligand Interaction by a Polymerized Bilayer Assembly", Science, vol. 261, Jul. 30, 1993, pp. 585–588, published by the American Association for the Advancement of Science (Washington, D.C.).

Cocchi, J.M. et al. "Comparison Between Direct Binding, Competition and Agglutination Assays in the Charactertization of Polyclonal Anti–idiotypes Against Anti–HBs Human Monoclonal Antibodies", Immunological Meth., vol. 160, 1993, pp. 1–9, Elsevier Science Publishers.

Kuby, J. Immunology, Second Edition (1994), pp. 147–150, W. H. Freeman and Company (New Yok, NY).

Cornell, B.A. et al. "A Biosensor that uses Ion–Channel Switches", Nature, vol. 387, Jun. 5, 1997, pp. 580–583, published by Nature Publishing (New York, NY).

Lin, V. et al., "A Porous Silicon–Based Optical Interferometric Biosensor", Science, vol. 278, Oct. 31, 1997, pp. 840–843, published by the American Association for the Advancement of Science (Washington, D.C.).

Pan, J.J. et al. "Molecular Recognition and Colorimetric Detection of Cholera Toxin by Poly(diacetylene) Liposomes Incorporating Gm 1 Ganglioside", Langmuir, vol. 13, No. 6, 1997, pp. 1365–1367, published by the American Chemical Society (Washington, D.C.).

Gupta, V. K. et al. "Optical Amplification of Ligand–Receptor Binding Using Liquid Crystals", Science, vol. 279, Mar. 27, 1998, pp. 2077–2080, published by the American Association for the Advancement of Science (Washington, D.C.).

Dancil, K.S. et al. "A Porous Silicon Optical Biosensor: Detection of Reversible Binding of IgG to a Protein A–Modified Surface", J. Am. Chem. Soc., vol. 121, 1999, pp. 7925–7930, published by the American Chemical Society (Washington, D.C.).

Kim, S–R., et al. "Orientation of Liquid Crystals on Mechanically Rubbed Films of Bovine Serum Albumin: A possible Substrate for Biomolecular Assays Based on Liquid Crystals", Anal. Chem., vol. 72, No. 19, Oct. 1, 2000, pp. 4646–4653, published by the American Chemical Society (Washington, D.C.).

* cited by examiner

IgG for VSV-I

FIG. 5

IgG + VSV-I

FIG. 6

(control)
IgG + VSV-NJ

METHOD AND APPARATUS FOR DETECTION OF MICROSCOPIC PATHOGENS

CROSS-REFERENCES TO RELATED APPLICATIONS

This application claims priority to U.S. Provisional Application No. 60/182,941, filed Feb. 16, 2000, the entire disclosure of which is incorporated herein by reference.

This invention was made with United States government support awarded by the following agency: ONR N00014-97-0702. The United States has certain rights in this invention.

FIELD OF THE INVENTION

This invention pertains generally to assay devices and methods for the detection of microscopic pathogens such as viruses or bacteria in a sample.

BACKGROUND OF THE INVENTION

Methods for detecting the presence of biological substances and chemical compounds in samples has been an area of continuous development in the field of analytical chemistry and biochemistry. Various methods have been developed that allow for the detection of various target species in samples taken from sources such as the environment or a living organism. Detection of a target species is often necessary in clinical situations before an illness may be diagnosed and a prescribed method of treatment may be undertaken.

Several types of assay currently exist for detecting the presence of target species in samples. One conventional type of assay is the radioimmunoassay (RIA). RIA is a highly sensitive technique that can detect very low concentrations of antigen or antibody in a sample. RIA involves the competitive binding of radiolabeled antigen and unlabeled antigen to a high-affinity antibody. Typically, the labeled antigen is mixed with the antibody at a concentration that just saturates the antigen-binding sites of the antibody molecule. Then, increasing amounts of unlabeled antigen of unknown concentration are added. Because the antibody does not distinguish between labeled and unlabeled antigen, the two types of antigen compete for the available binding sites on the antibody. Measuring the amount of labeled antigen free in solutions, it is possible to determine the concentration of unlabeled antigen. Kuby, J., *Immunology*, W. H. Freeman and Company, New York, N.Y. (1991), pp. 147–150.

Another type of assay which has become increasingly popular for detecting the presence of pathogenic organisms is the enzyme-linked immunosorbent assay or ELISA. This type of assay allows pathogenic organisms to be detected using biological species capable of recognizing epitopes associated with proteins, viruses and bacteria. Generally, in an ELISA assay, an enzyme conjugated to an antibody will react with a colorless substrate to generate a colored reaction product if a target species is present in the sample. Kuby, J., Immunology, W. H. Freeman and Company, New York, N.Y. (1991), pp. 147–150. Physically adsorbed bovine serum albumin has been used in various such assays as a blocking layer because it has been found to prevent the non-specific adsorption of biological species that might interfere with or result in erroneous assay results.

Although ELISA and other immunosorbent assays are simple and widely used methods, they have several disadvantages. Tizard, I. R. *Veterinary Immunology: An Introduction*, W.B. Saunders Company, Philadelphia, Pa. (1996); Harlow, Ed.; Lane, D. *Antibodies: A Laboratory Manual*, Cold Springs Harbor Laboratory, Cold Springs Harbor, N.Y. (1988); Van Oss, C. J.; van Regenmortel, M. H. V. *Immunochemistry*, Dekker, New York, N.Y. (1994). Labeled antibodies can be expensive, especially for assays requiring radioactive labels. Additionally, radioactive labels require special handling as radioactive materials are also hazardous. The labeling of a compound, which is the main drawback of these methods, may alter the binding affinity of antibody to analyte. Enzymes are large molecules that may sterically inhibit antibody activity or it may lose enzymatic activity after conjugation to antibodies. Another concern with immunosorbent assays is non-specific binding of proteins to the solid support, antigen, and antibody complexes. This can lead to an increase in background noise, loss of sensitivity, and potentially a false positive test result. Additionally, the immobilization of proteins on the solid support can affect the conformation of the binding sites, leading to a decrease in sensitivity, and possible increase in non-specific binding. For example, physical adsorption of proteins to polystyrene wells occurs due to hydrophobic interactions between the protein and solid support. These interactions can also promote unfolding of the amino acid chains in order to cover the polystyrene surface. This can lead to possible inactivation of the binding sites.

Qualitative diagnostic assays based on aggregation of protein coated beads can also be used for the detection of proteins and viruses. Tizard, I. R. *Veterinary Immunology: An Introduction*, W.B. Saunders Company, Philadelphia, Pa. (1996): Cocchi, J. M.; Trabaud, M. A.; Grange, J.; Serres, P. F.; Desgranges, C. *J. Immunological Meth.*, 160, (1993), pp. 1; Starkey, C. A.; Yen-Lieberman, B.; Proffitt, M. R. *J. Clin. Microbiol.*, 28, (1990), pp. 819; Van Oss, C. J.; van Regenmortel, M. H. V. *Immunochemistry*, Dekker, New York, N.Y. (1994). For direct detection of antibodies, antigen is non-specifically adsorbed to the surface of latex beads which are several microns in diameter. The protein-coated beads possess a slight charge which prevents aggregation. Introduction of an antibody specific to the adsorbed protein can link the beads, leading to agglutination. The agglutination can be detected by eye or by other methods such as quasi-elastic light scattering. Visual agglutination assays, however, are not sensitive and measurement by quasi-elastic light scattering requires complex apparatus and is not suitable for use in locations remote from central labs. Furthermore, it is not possible to perform highly multiplexed agglutination assays using microarrays because of the bulk solution methodology of this type of assay.

To overcome the need for labeled proteins, principles based on direct detection of the binding of proteins and ligands have been investigated. Schmitt, F.-J.; Haussling, L.; Ringsdorf, H.; Knoll, W. *Thin Solid Films*, 210/211, (1992), pp. 815; Hauslling, L.; Ringsdorf, H. *Langmuir*, 7, (1991), pp. 1837. Surface plasmon reflectometry (SPR) is one such method. SPR is sensitive to changes in the index of refraction of a fluid near a thin metal surface that has been excited by evanescent electromagnetic waves. The binding of proteins to ligands can be detected by examining an increase in the resonance angle or intensity of signal. Typical angular resolution using this method is 0.005° allowing detection of sub-angstrom changes in adsorbed film thickness with SPR. However, care must be taken to ensure that the change in resonance angle is due to binding and not just a change in the bulk solution index of refraction. A thermally stable environment is required due to the dependence of the resonance angle on the index of refraction of the fluid. An increase in temperature from 25° C. to 26° C. in water amounts to a change in the index of refraction by 0.0001. This increase would result in the change in resonance angle of approximately 0.015° or roughly 0.2 nm in the observed height of a protein layer. This temperature stability requirement makes SPR unsuitable for most field applications. In addition, non-specific adsorption of molecules on to or near the sensor surface can lead to false changes in signal, requiring a surface which minimizes non-specific interactions. Therefore, surface plasmon reflectivity is more complex than ELISA, requires laboratory based equipment, and the preparation of a well defined surface.

The use of ion-channel switches for detecting biospecific interactions has been reported. Cornell, B. A.; Braach-Maksvytis, V. L. B.; King, L. G.; Osman, P. D. J.; Raguse, B.; Wieczorek, L.; Pace, R. J. Nature, 387, (1997), pp. 580. In a device using ion channel switches, a tethered lipid membrane incorporating mobile ion channels is separated from a gold electrode surface by an ion reservoir. The gold surface serves as an anchor for the membrane and acts as an electrode. Within the membrane are upper and lower ion channels. In order to become conductive, the outer and inner ion channels must align and form a dimer. Membrane spanning lipids, which help stabilize the lipid membrane, are attached at one end to the electrode surface and are terminated with ligands that extend away from the membrane. The ion channels of the outer layer possess ligands. Unbound, the outer ion channels move freely, occasionally forming dimers with the inner channels, allowing conduction. The binding of a bivalent molecule to both the ion channel and membrane spanning lipid restricts the mobility of the outer ion channel, leading to a measurable decrease in conductivity. However, if a large amount of protein adsorbs to the outer layer, the ion channel mobility presumably would be restricted and a false decrease in conductance could be observed due to non-specific interactions. Additionally, this method requires sensitive devices for detecting the change in conductance. The procedure for fabricating the membranes requires several hours and the membrane stability is limited (must be immersed in solution). More importantly, specific antibodies must be attached to the membrane/channels, requiring separate protein chemistry for each analyte to be detected.

A method based on a porous silicon support that permits optical detection of the binding of specific proteins to ligands has been reported. Lin, V.; Motesharei, K.; Dancil, K. S.; Sailor, M. J.; Ghadiri, M. R. Science, 278, (1997), pp. 840; Dancil, K. S.; Greiner, D. P.; Sailor M. J. *J. Am. Chem. Soc.*, 121, (1999), pp. 7925. The porous areas are typically 1 to 5 µm deep and a few square micrometers to millimeters in area. Typical binding times are on the order of 30 minutes followed by rinsing of the surface. Initial work in this area incorrectly reported the detection of extremely low concentrations of analyte. Binding of streptavidin to biotinylated surfaces was initially found to reduce the index of refraction of the porous support, however this was later correctly attributed to an oxidation of the surface. In addition, a change in the effective optical thickness of the film was reportedly observed upon introduction of streptavidin, however they could not differentiate between specific interactions and non-specific adsorption. This method does not require labeled molecules, however, the porous silicon surface is susceptible to oxidation and non-specific adsorption.

The use of polymerized multilayer assemblies for the detection of receptor-ligand interactions has also been reported. Charych, D. H.; Nagy, J. O.; Spevak, W.; Bednarski, M. D. *Science*, 261, (1993), pp. 585; Pan, J. J.; Charych, D. *Langmuir*, 13, (1997), pp. 1365. Polydiacetylene multilayer films deposited by Langmuir-Blodgett technique change color from blue to red due to a conformational change in the polymer backbone. For example, changes in temperature or pH can cause a shift in color. The response can be controlled and used for protein detection by attaching ligands to the multilayer. Upon binding of a multivalent macromolecule to ligands, stress is introduced into the multilayer assembly. A change in color is seen in the system if sufficient protein is bound, with binding times typically on the order of 30 minutes. This system permits direct detection of receptor-ligand interactions and transduces the events into an optical signal that can be easily measured and quantified. The optical output can be interpreted by eye or analyzed with a spectrophotometer for quantitative conclusions. The use of polymerized multilayer assemblies for the detection of influenza virus has been demonstrated. A significant disadvantage of this method, however, is that it requires multi-valent analyte. Multiple ligands connected to the polymerized multilayer must attach to the same macromolecule. This prevents the use of this method for monovalent molecules (even bead based assays can be performed competitively, not requiring multivalent molecules). Binding of bivalent molecules such as IgG's has not been demonstrated. Furthermore, Langmuir-Blodgett deposition is a process which is difficult to translate from laboratory to commercial scale. As an alternative method to Langmuir-Blodgett deposition, these principles has also been demonstrated using vesicles. However, research based on vesicles, reveals the usefulness of the system to be limited because it is insensitive to the analyte at concentrations below 0.1 mg/ml.

Although many of the conventional assay methods described above work very well to detect the presence of target species, many conventional assay methods are expensive and often require instrumentation and highly trained individuals, which makes them difficult to use routinely in the field. Thus, a need exists for assay devices and systems which are easier to use and which allow for evaluation of samples in remote locations.

Recently, assay devices that employ liquid crystals have been disclosed. For example, a liquid crystal assay device using mixed self-assembled monolayers (SAMs) containing octanethiol and biotin supported on an anisotropic gold film obliquely deposited on glass has recently been reported. Gupta, V. K.; Skaife, J. J.; Dubrovsky, T. B., Abbott N. L. *Science*, 279, Mar. 27, 1998, pp. 2077–2079. In addition, PCT publication WO 99/63329 published on Dec. 9, 1999 discloses assay devices using SAMs attached to a substrate and liquid crystal layer which is anchored by the SAM. Although the disclosed liquid crystal-based assay devices which use anisotropic gold films are suitable for use in determining whether a target protein is present in a sample, the preparation of the anisotropic gold film by oblique deposition is difficult. For example, the preparation of the obliquely deposited gold films requires complicated cleaning steps and high vacuum deposition. Further, such assay devices are suited to the detection of protein molecules in a sample rather than larger complex particles such as viruses and other pathogens.

SUMMARY OF THE INVENTION

In accordance with the present invention, microscopic pathogens such as bacteria and viruses may be detected in a simple and efficient manner. The detection of a pathogen can be carried out by personnel who have minimal training and without requiring specialized laboratory facilities or equipment. Detection is provided with accurate readout in a manner that is faster than conventional serological tests. It is possible to screen for multiple microscopic pathogens in a single test.

A detection apparatus in accordance with the invention includes a substrate having a detection region thereon comprising microstructures which include depressions of width and depth sized to align liquid crystal material in contact therewith. The depressions are also sized to be occupied by the pathogen to be detected. The depressions may comprise parallel microgrooves. For detection of viruses, the width and depth of the microgrooves will generally be on the order of 5 nm to 500 nm, while for detection of bacteria the width and depth of the microgrooves will generally be on the order of 0.1 $\mu$m to 10 $\mu$m. The microstructure on the substrate may be formed by various suitable technologies, including molding a hardenable polymer material, utilizing a micromachined mold, and by other methods such as mechanical embossing or by using an elastomeric material such as polydimethylsiloxane to form a replica from a master and then using the elastomeric replica to form replicas from other polymeric materials including polyurethane, polycyanoacrylate, and polystyrene. The surface of the detection region is treated to block nonspecific binding of pathogens to the surface and includes a binding agent that specifically binds the selected pathogen to be detected.

The detection apparatus may be further embodied in that at least a portion of the detection region may be coated with an inorganic material such as an oxide of silicon, an oxide of a metal, a metal, or combinations of these. A metal coated region such as a gold or silver coated region may include a region that is the reaction product of the metal coated region with a mercaptan or a disulfide. In still other embodiments, substantially all the binding agent is located in the depressions on the surface of the detection region.

To test a sample for the presence of the selected pathogen, the sample is contacted to the surface of the detection region to permit the pathogen particles, if present, to be bound to the surface by the binding agents and to occupy the depressions. A liquid crystal material is thereafter applied to the detection region that will be aligned by the microstructures on the surface of the substrate in the absence of binding of particles to the surface. Where no particles are present on the surface, the liquid crystal material is aligned and appears uniform and dark when visually examined, typically by utilizing an appropriate polarizing viewing material. If the specific pathogen is present in the sample, it will be bound to the binding agents and will substantially occupy the depressions on the surface of the substrate. The occupation of the depressions by the particles disrupts the uniform alignment of the liquid crystal material, with the result that the detection region appears relatively brightly colored when viewed with the appropriate polarizing material. In this manner, an observer can readily and easily determine whether or not the specific pathogen is present in the sample. The depressions on the substrate are sufficiently large compared to molecular material such as proteins which may be bound to the surface, and thus the non-specific binding of proteins or other molecular materials does not disrupt the uniform alignment of the liquid crystal material.

Multiple substrates can be used or the surface of the detection region of a single substrate may be patterned such that the various areas of the detection region each have a binding agent for a different specific pathogen. This allows a single sample to be simultaneously checked for the presence of a variety of pathogens. The detection apparatus may further be embodied in a microarray in which multiple detection regions are provided on a unitary substrate to facilitate the screening of a sample for the presence of several pathogens. Additionally, the detection apparatus may be further embodied in that it contains two or more detection regions such that the detection regions have grooves of different widths, depths or both such that the different regions of the detection apparatus have different sensitivities to a single specific pathogen.

An exemplary material that may be used to block non-specific absorption of viruses is bovine serum albumin (BSA). An exemplary binding agent is an immunoglobulin or portion thereof or an antibody or portion thereof selected for binding to a specific virus. However, it is understood that any suitable blocking layer material and binding agent may be utilized in the present invention.

In further embodiments of the invention, magnetic beads may be used in conjunction with the detection apparatus and methods of the present invention. In such embodiments, the surface of the beads may include a binding agent that binds a selected pathogen. The beads may be contacted with a sample and subsequently contacted with the detection region. If the pathogen is present in the sample, it will bind to the surface of the beads such that the bead binds to the binding agent in the detection region of the detection apparatus.

Further objects, features and advantages of the invention will be apparent from the following detailed description when taken in conjunction with the accompanying drawings.

BRIEF DESCRIPTION OF THE DRAWINGS

In the drawings:

FIG. 5 is a schematic view illustrating the blocking layer including blocking molecules and the binding agent molecules on the surface of the substrate with no virus present.

FIG. 6 is a schematic view similar to that of FIG. 6 illustrating the binding of a specific virus to the substrate.

FIG. 7 is a schematic view similar to that of FIG. 6 showing the presence of a virus particle which is not bound to the binding agent on the surface of the substrate.

FIG. 8 is a simplified perspective view of a detection apparatus having an array of detection regions which each bind a different specific pathogen.

DETAILED DESCRIPTION OF THE INVENTION

Figure 1:
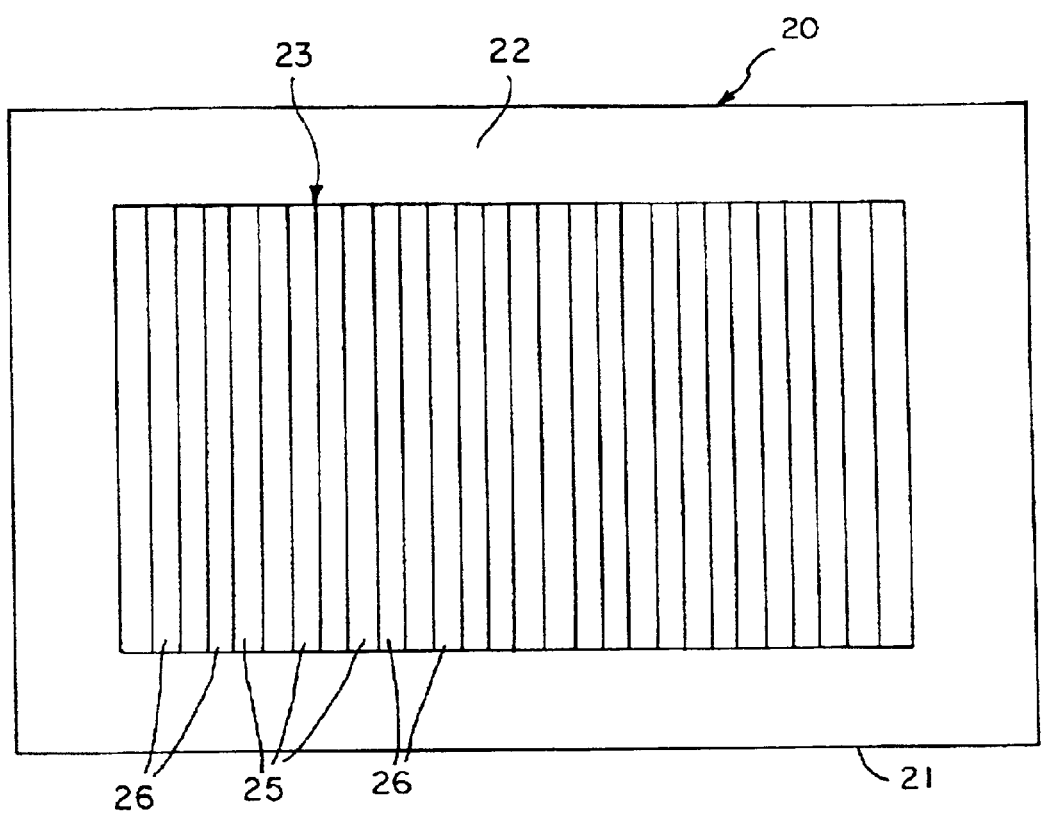
FIG. 1 is a simplified plan view of a detection apparatus having a detection region in accordance with the invention.

The present invention may be utilized particularly for the detection of pathogens such as specific strains of a virus in a simple and efficient manner. Both naturally occurring and genetically engineered pathogens pose a significant human and animal health risk, which can be dramatically reduced by rapid detection. Agencies as diverse as the World Health Organization, the Centers for Disease Control, and the U.S. Departments of Defense and Agriculture all stress the importance of rapid and accurate information at the earliest stage of a potential public health emergency to inform decision-making at the local and international levels. The present invention is well suited to meet such needs. It can be used in the field without the need for a laboratory or specially trained personnel. It provides an accurate read-out faster than conventional serological tests such as serum neutralization (SN), complement fixation (CF), hemagglutination inhibition (HI), single radial hemolysis (SRH), counter immunoelectrophoresis (CIEOP), fluorescent antibody (FA), or ELISA. The invention may be embodied in an addressable microarray, allowing a sample from a patient or from the environment to be simultaneously probed for a very broad spectrum of pathogenic agents. Moreover, by immobilizing antibodies to viral, rickettsial, and bacterial surface proteins, it is possible to identify tissue targets and routes of entry of weaponized recombinant organisms faster than genetic analyses. The detection apparatus may also serve as a "pre-screening front-end" to more complex devices with embedded cells capable of detecting both biological and chemical agents.

Foot and mouth disease virus is an example of an animal pathogen whose importation, possession, or use is prohibited under USDA regulations. This agent has also been identified as a likely candidate for weaponization. Vesicular stomatitis virus (VSV) causes a clinically indistinguishable, non-fatal infection in cattle and is responsible for frequent epizootics in North and South America. In both diseases oral lesions contain large numbers of virions. With antibodies against VSV-NJ, VSV-Indiana, and foot and mouth disease virus immobilized on the detection apparatus of the invention, veterinarians in the field can make immediate diagnosis, minimizing herd loss and zoonotic risk.

Bronchoalveolar lavage is a procedure performed in patients with pulmonary syndromes in order to obtain a rapid viral diagnosis of cytomegalovirus. In performing this procedure, parainfluenza, influenza, and enteroviruses have also been detected. The amount of material recovered from a single procedure is small and each viral test requires a separate sample. The present invention may be used for simultaneous detection of all these pathogens, as well as bacterial agents such as *L. pneumophila, M. tuberculosis*, or atypical mycobacterial agents, e.g., M. kansaii or M. avium. For minimal additional cost, a range of rare, often overlooked, causative agents can be included in the same assay with the more probable candidates.

Figure 2:
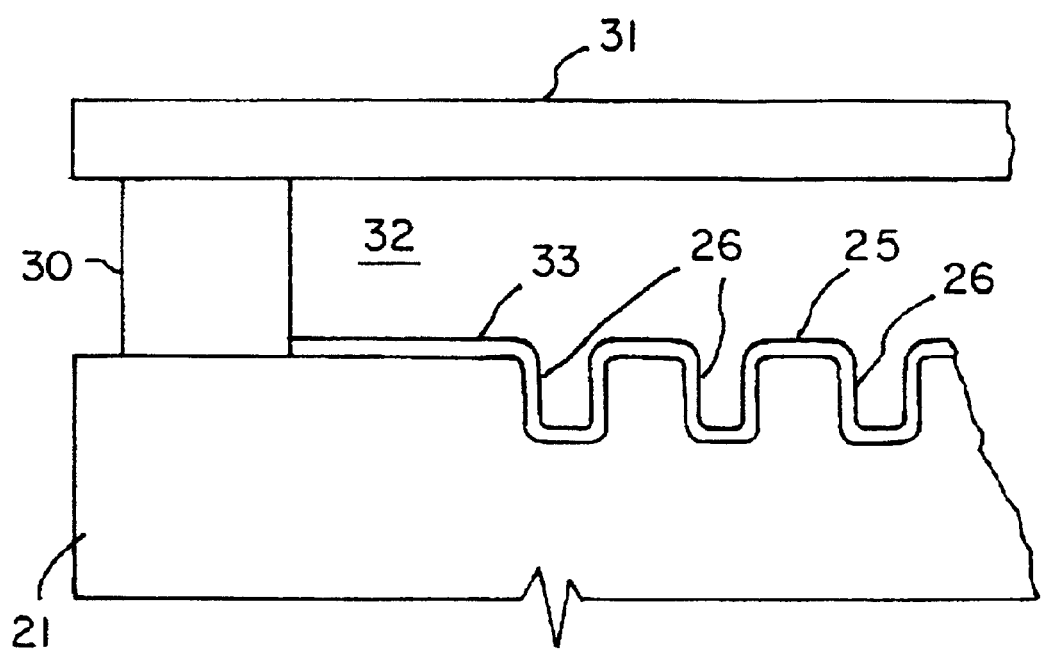
FIG. 2 is a simplified cross-sectional view of a detection apparatus in accordance with the invention.

For purposes of exemplifying the invention, a simplified plan view of the substrate of a detection apparatus in accordance with the invention is shown generally at 20 in FIG. 1. The substrate 21 is formed of a base plate of material, e.g., a polymeric plastic, preferably having a flat top surface area 22 which surrounds a detection region 23. As discussed further below, the detection region 23 is formed of a microstructure having depressions, which as shown in FIGS. 1 and 2, may comprise adjacent ridges 25 separating depressions, preferably grooves 26, with the grooves disposed parallel to one another across the detection region 23. The width and depth of the grooves 26, and the spacing between the grooves as defined by the tops of the ridges 25, are selected to cause liquid crystal material to adopt a uniform orientation that is impressed upon it by the grooves and ridges. The size of the grooves and the spacing of the grooves are also selected such that adherence of a pathogen particle or clumps of particles of appropriate size will disrupt the uniform orientation of the liquid crystal material, causing a visible change in the appearance of a liquid crystal to signal the detection of the virus to an observer. Various conventional liquid crystal materials may be utilized, including nematic and smectic liquid crystal. The liquid crystals may be thermotropic or lyotropic phases. In general, groove widths and depths which are suitable to be occupied by viruses will be in the range of 5 to 500 nanometers (nm) and suitable spacing of the grooves 26 by the ridges 25 may also be in the same range. Where the selected pathogen is a bacteria, the width and depths of the grooves will generally be in the range of 0.1 micrometer ($\mu$m) to 10 $\mu$m to allow the grooves to be occupied by the bacteria. The grooves may be of various geometries, e.g., square, rectangular, triangular, or semicircular, and typically will be formed somewhat rounded or wedge shaped at nano-dimensions. The width of the grooves is preferably selected to be about the size of an individual pathogen particle, so that the particle will fit at least partially into a groove to occupy the groove. The depressions 26 may be formed in geometries other than linear, parallel grooves, e.g., as ellipsoids, truncated grooves, mixtures of grooves of different width, depth and shape, selected to act on the liquid crystal to orient it in the desired uniform orientation.

The apparatus of the present invention may utilize the grooved substrate by itself in the form 20 shown in FIG. 1. The apparatus of the invention may also be utilized with a cover panel to cover the liquid crystal material, as further illustrated in the cross-sectional view of FIG. 2. The substrate 21 is formed in the same manner as described above, having the grooves 26 spaced by ridges 25 of selected and controlled dimensions. A spacer or gasket 30 is mounted on the non-textured surface 22 to fully or partially surround the detection region 23 and to support a cover plate 31. The substrate 21, spacer 30 and cover plate 31 enclose a volume 32 which can contain the liquid crystal material.

The exposed surfaces of the ridges 25 and the grooves 26 may comprise or be covered with a layer 33 of material that functions as a blocking layer to prevent nonspecific adsorption of viruses, bacteria, or other pathogens onto the surfaces. An exemplary blocking layer material comprises a bovine serum albumin (BSA) film. The blocking layer may be formed from albumins from other animals, as well as by immobilization of polyethyleneoxide on the surface of the substrate. Zwitterionic polymers will also lower non-specific adsorption. The material of the substrate itself may also be selected to prevent non-specific adsorption of pathogens. As a further example, the polymer of the substrate may be derivatized using oligoethylene glycol strands to prevent non-specific adsorption. In accordance with the invention, a binding agent on the detection region surface in or on the layer 33 specifically binds the virus to be detected. The layer 33 is selected such that it does not by itself disrupt the uniform orientation of the liquid crystal material.

The substrate may be formed from various materials including any polymer that is stable upon exposure to water. Examples include, but are not limited to, polystyrene, polymethylmethacrylate, polycarbonate, polycyanoacrylate, polyurethane, and polyimides. One preferred group of substrates are formed from polyurethane, polycyanoacrylate, or polystyrene. Polystyrene is an especially preferred substrates for use in the present invention. An alternative is a spin-on glass, e.g., silica material formed through wet chemical, sol-gel methods, such as tetraethoxysilane (TEOS). This inorganic material may be molded. Because it is a glass presenting hydroxyl groups, one could treat the surface using silane chemistry (e.g., 3-aminopropyl triethoxysilane (APES)). Because it is rigid, it may be less prone to "rounding" of grooves, etc. than an elastomer.

The topography of the substrate and detection region of the detection apparatus may be modified by coating at least a portion of the detection region with an inorganic material such as, but not limited to, an oxide of silicon, an oxide of a metal, a metal, combinations of these. Preferably, this is accomplished using vacuum deposition techniques such as described below. Silver and gold are particularly preferred inorganic materials for use in such topography modification, and gold is especially preferred. When at least a portion of the detection region is coated with gold or silver, they may be treated with an organosulfur compound such as a mercaptan or disulfide which will bind to the metal surface.

The substrate with microstructures including depressions formed therein may be produced by various manufacturing processes. In one suitable process, a mold is formed by conventional micromachining processes, e.g., in a silicon workpiece, which then has a liquid polymer applied to it which is solidified. Mechanical embossing of a polymer similar to that used in the production of compact discs and holographic gratings may also be used. A hot, hard master is pressed into a polymer sheet heated to about its glass transition temperature, transferring the relief in the master to the polymer, and the polymer is then cooled below its glass transition temperature before removal of the master. Substrates may also be prepared by photopolymerization techniques.

In one preferred method for preparing a substrate, a silicon or other master is used to form a polydimethylsiloxane (PDMS) or other elastomeric replica. Preferably, a fluorine-containing compound is applied to the surface of the silicon master prior to making the elastomeric replica such that removal of the elastomeric replica is easier. The elastomeric replica is then preferably used as a master to form a replica from a thermally-curing material such as, but not limited to epoxide or more preferably from a ultraviolet-curing material such as, but not limited to polyurethane, polycyanoacrylate, or polystyrene. Polystyrene is an especially preferred material for use in forming such a polymeric replica.

The binding agents may comprise various suitable biomolecule recognition agents, including peptides and polypeptides; RNA and DNA oligomers; biotin; avidin; sugars; antibodies; FAB and FAB' or other active fragments of antibodies such as, but not limited to, immunoglobulins, such as but not limited to, IgG; small molecules (e.g., drugs) tethered to the surface of the substrate (permitting screening of small molecule/protein-virus interactions for drug research), and the polymer material may be a functional polymer that presents a ligand that binds a virus or a reactive moiety that can be used to covalently attach a binding agent (e.g., an SH group). Immunoglobulins including IgG, IgA, IgM, IgD, and IgE, and fragments of immunoglobulins are preferred binding agents, and IgG and fragments of IgG are especially preferred binding agents.

The binding agent may be distributed over the surface and depressions of the detection region. However, substantially all of the binding agent may be located in the depressions or more preferably, the grooves of the detection region of the detection apparatus. This may be accomplished by stamping the top of the ridges with a blocking compound such as BSA and then treating the detection region with a binding agent. Although some of the binding agent may be adsorbed onto non-depression areas of the detection region, this method provides a detection apparatus with the majority of the binding agent located in the depressions.

For purposes of exemplifying the invention, a simplified plan view of the substrate of a detection apparatus in accordance with the invention is shown generally at 20 in FIG. 1. The substrate 21 is formed of a base plate of material, e.g., a polymeric plastic, preferably having a flat top surface area 22 which surrounds a detection region 23. As discussed further below, the detection region 23 is formed of a microstructure having depressions, which as shown in FIGS. 1 and 2, may comprise adjacent ridges 25 separating depressions, preferably grooves 26, with the grooves disposed parallel to one another across the detection region 23. The width and depth of the grooves 26, and the spacing between the grooves as defined by the tops of the ridges 25, are selected to cause liquid crystal material to adopt a uniform orientation that is impressed upon it by the grooves and ridges. The size of the grooves and the spacing of the grooves are also selected such that adherence of a pathogen particle or clumps of particles of appropriate size will disrupt the uniform orientation of the liquid crystal material, causing a visible change in the appearance of a liquid crystal to signal the detection of the virus to an observer. Various conventional liquid crystal materials may be utilized, including nematic and smectic liquid crystal. The liquid crystals may be thermotropic or lyotropic phases. In general, groove widths and depths which are suitable to be occupied by viruses will be in the range of 5 to 500 nanometers (nm) and suitable spacing of the grooves 26 by the ridges 25 may also be in the same range. Where the selected pathogen is a bacteria, the width and depths of the grooves will generally be in the range of 0.1 micrometer ($\mu$m) to 10 $\mu$m to allow the grooves to be occupied by the bacteria. The grooves may be of various geometries, e.g., square, rectangular, triangular, or semicircular, and typically will be formed somewhat rounded or wedge shaped at nano-dimensions. The width of the grooves is preferably selected to be about the size of an individual pathogen particle, so that the particle will fit at least partially into a groove to occupy the groove. The depressions 26 may be formed in geometries other than linear, parallel grooves, e.g., as ellipsoids, truncated grooves, mixtures of grooves of different width, depth and shape, selected to act on the liquid crystal to orient it in the desired uniform orientation.

Magnetic beads may be used in conjunction with the detection apparatus to determine whether a pathogen is present in a sample. When magnetic beads are used they are typically contacted with an aqueous solution of the sample. Biochemical materials in the sample will be adsorbed onto the surface of the magnetic beads. Therefore, if the pathogen is present, it will also be adsorbed onto the surface of the beads. The surfaces of the magnetic beads may include a binding agent to increase the binding of the pathogen to the magnetic beads. In either case, if the pathogen is present in the sample, then the beads with the adsorbed pathogen will bind to the binding agent in the depressions of the detection region. A magnet may be used to initially draw the beads into the grooves. When magnetic beads are to be used in conjunction with a detection apparatus, the depressions or grooves in the detection region should be suitably sized so that the bead with the bound pathogen can fit into the grooves or depressions.

Figure 3:
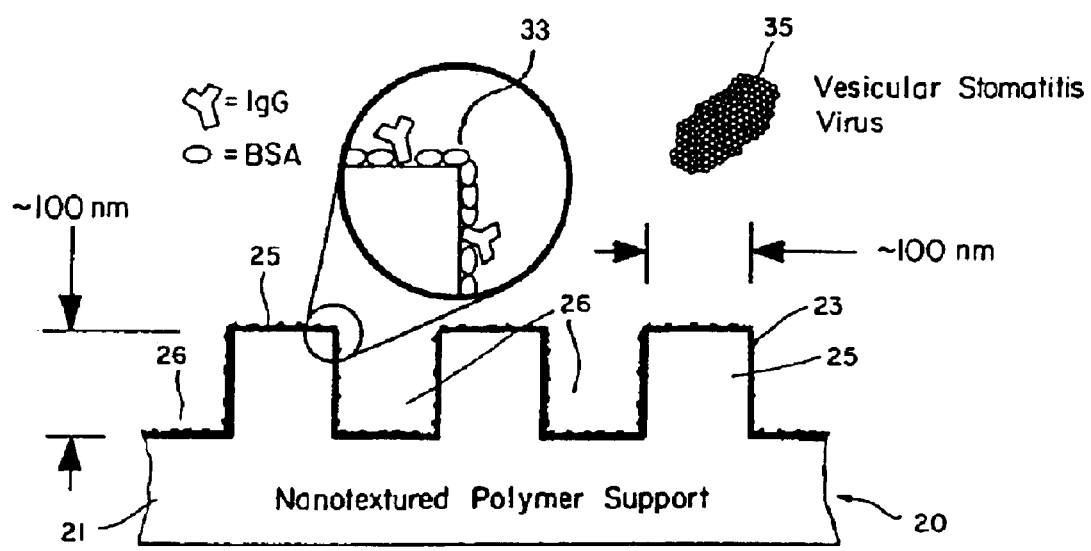
FIG. 3 is a schematic cross-sectional view illustrating the substrate of the detection apparatus with a blocking layer including binding agents therein for binding to a specific pathogen.
Figure 4:
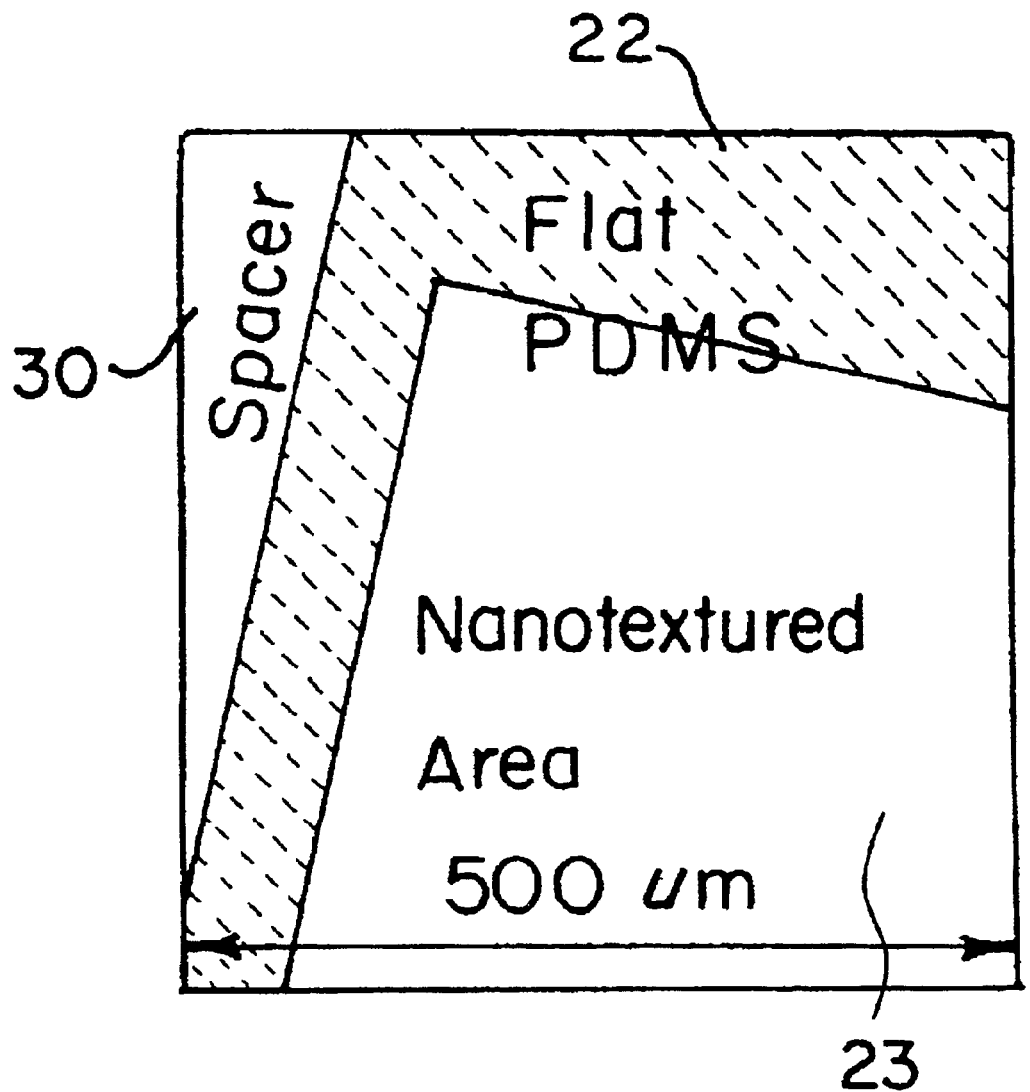
FIG. 4 is an illustrative view of a substrate showing the relative position of the detection region.
Figures 5, 6:
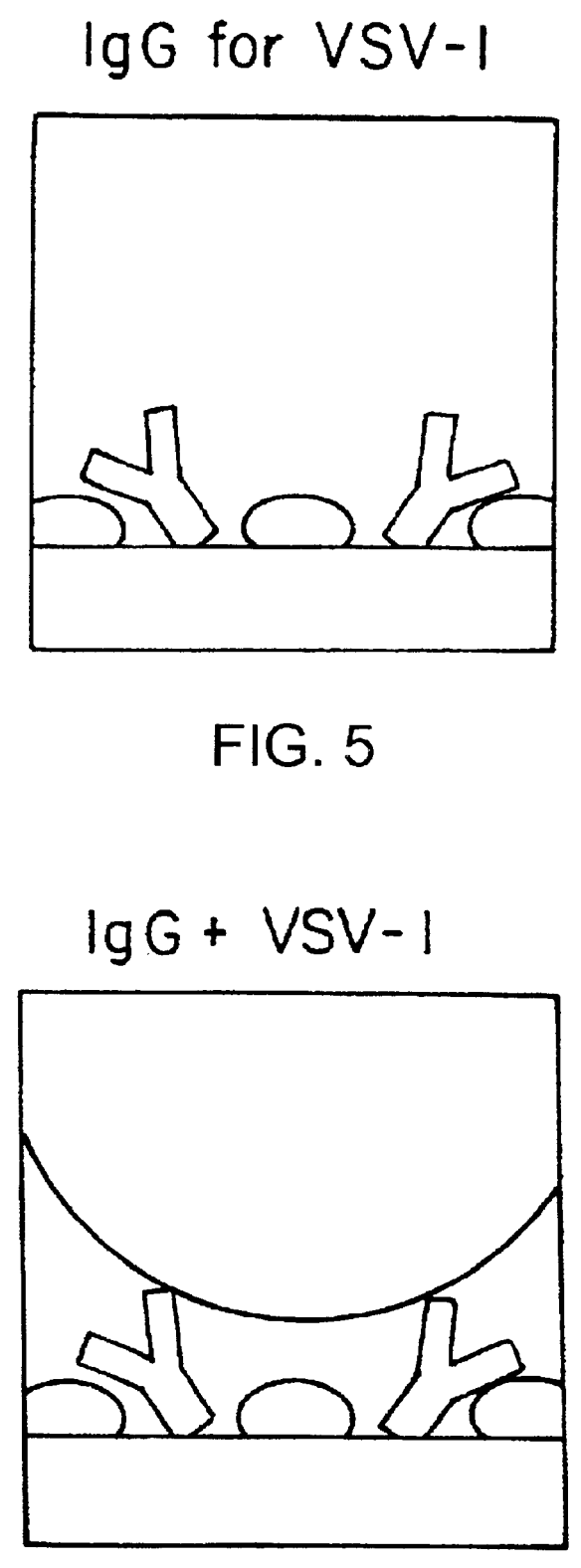

An example of the invention will now be described with reference to FIGS. 3–8. This example utilized an elastomeric substrate 21 formed by nanoscale molding of polydimethylsiloxane, using as a mold the surface of a silicon wafer that was patterned with grooves having approximately 100 nm width and depth and 100 nm spacing that were formed by using e-beam lithography. The resulting microstructure with substantially square grooves and ridges of 100 nm dimensions is illustrated in the simplified cross-sectional view of FIG. 3. Atomic force microscopy and scanning electron microscopy confirmed that the nanometer-scale topography of the silicon template was reproduced into the polymeric material. A layer 33 of BSA (as a blocking layer) and immunoglobulin G (IgG) (as a binding agent) was formed in a film on the surfaces of the grooves 26 and the ridges 25 in the detection region. One skilled in the art will recognize that portions or fragments of immunoglobulins may be used in place of the whole immunoglobulin. As shown in FIG. 3 for illustration, the size of the BSA and IgG molecules adhered to the surfaces to form the layer 33 was small in comparison to the dimensions of the grooves 26. The dimensions of the grooves 26 were comparable in size to vesicular stomatitis virus (VSV) (typically virus particle size about 100 nm×45 nm), a particle of which is shown for illustration at 35 in FIG. 3. To form the layer 33, the patterned substrate 21 is sequentially immersed first in an aqueous solution of IgG and then in an aqueous solution of BSA. The resulting layer of molecules on the substrate surface is schematically illustrated in FIG. 5. When the substrate 21 with the layer 33 formed in this manner had a layer of liquid crystal material placed on it, the detection region in which the nanometer-scale grooves were formed caused the liquid crystal to appear uniformly dark when viewed between cross-polarizing sheets (with the grooves parallel to the analyzer). A commercially available liquid crystal material was utilized, 4-cyano-4'-pentylbiphenyl (5CB) nematic liquid crystal manufactured by BDH and available from EM Industries, Hawthorne, N.Y. (Other liquid crystal materials may be used, including smectic liquid crystals such as 8CB.) FIG. 4 shows the nano-textured detection region 23, the flat untextured area 24, and the region of the spacer 30. A photograph through the analyzer showed that the detection region 23 appeared uniformly dark due to uniform anchoring of the liquid crystal whereas the flat regions 22 of the substrate surface that do not have grooves were brightly colored because there are nc grooves arid the liquid crystal is not uniformly anchored on the surface. Thus, the presence of the nanoscale grooves 26 in the surface of the substrate in the detection region cause the liquid crystal to adopt a uniform orientation which is not erased by the adsorption of the BSA and IgG onto the substrate surface in the layer 33.

Figures 7, 8:
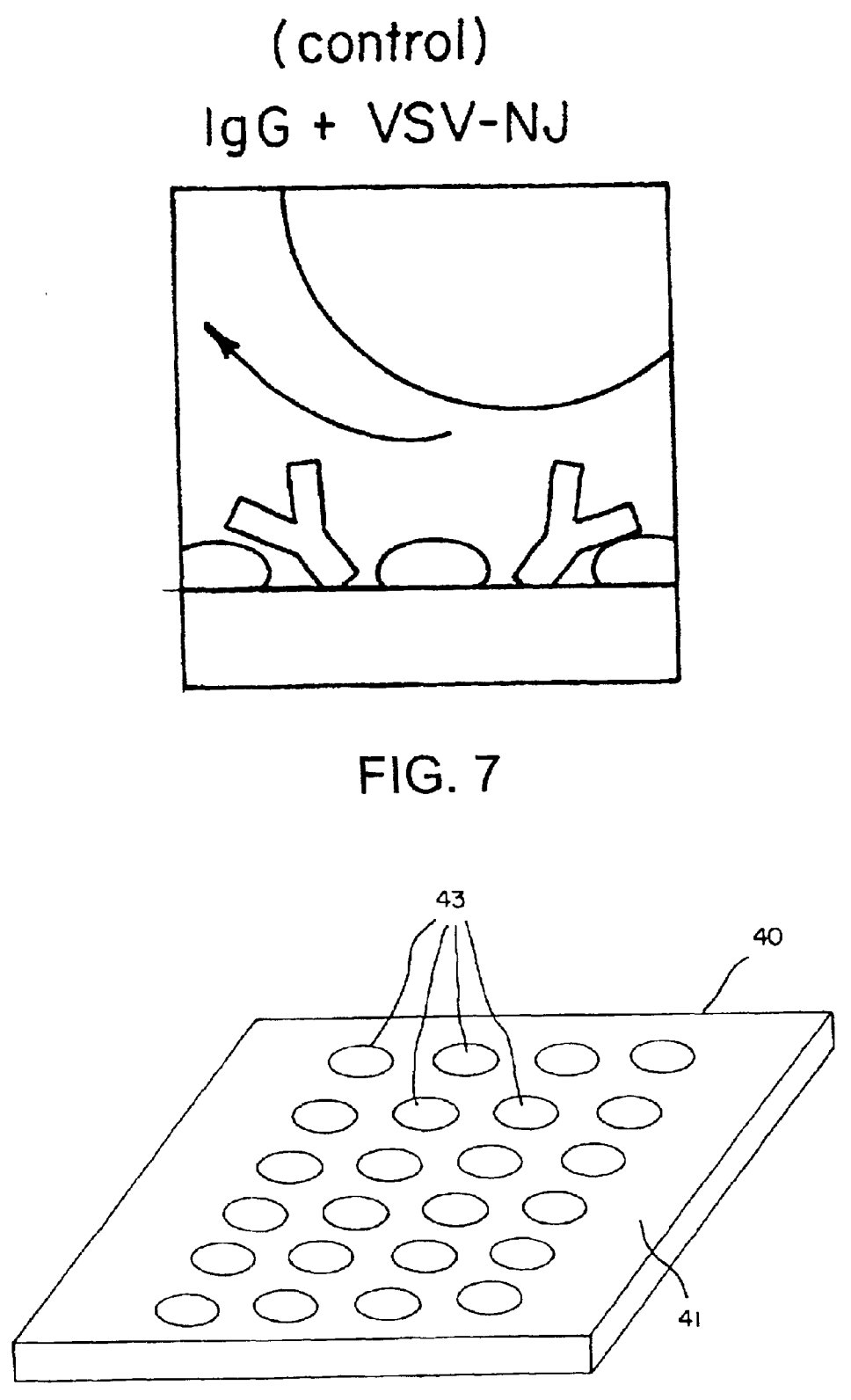

FIGS. 5–7 schematically illustrate the results of an example utilizing such a substrate in combination with liquid crystals to detect the presence of a specific strain of virus, the Indiana strain of VSV. The surfaces of the substrate 21 with the grooves 26 formed therein was pretreated as described above to form a layer 33 of BSA and IgG, the IgG selected to specifically bind to the Indiana strain of VSV (i.e., anti-VSV-I IgG), as illustrated schematically in FIG. 5. The width of the grooves 26 in the substrate was 100 nm, which is on the order of the size of the VSV virus particle (about 100 nm×45 nm), allowing the virus particle to at least partially fit into and occupy the groove. A photograph and observation of the detection region only which has the liquid crystal 5CB in contact therewith, showed a uniform dark appearance indicating the uniform anchoring of the liquid crystal to the substrate surface in the detection region. Another substrate similarly pretreated with BSA and anti-VSV-I IgG then was treated by placing a droplet of buffer containing the Indiana strain of VSV onto the surface of the substrate. The droplet was confined between a glass cover slip and the surface of the substrate. The cover slip was then removed, the surface of the substrate was rinsed with phosphate buffered saline (PBS), then placed under a stream of nitrogen to displace excess PBS, and then contacted with 5CB liquid crystal. When the droplet of buffer contained about 106 pfu/ml of VSV-I, the VSV-I was bound to the IgG, as illustrated schematically in FIG. 6, and the liquid crystal in contact with the surface then appeared non-uniform and bright. This result indicates that the presence of the virus erases the effect of the nanoscale grooves 26 on the alignment of the liquid crystal. A further experiment was performed utilizing the New Jersey strain of VSV, which does not bind to the IgG that is specific to the Indiana strain, as illustrated schematically in FIG. 7. When the substrate treated in this manner had liquid crystal applied to it, the uniform orientation of the liquid crystal was not substantially altered. The above results demonstrate that the detection system may be used to identify the presence of the Indiana strain of VSV in a sample and that the detection apparatus can differentiate between different strains of the same virus. Thus, the assay is specific to the Indiana strain of VSV.

The detection apparatus of the invention may also be incorporated in a "microarray" in which multiple separated detection regions are formed on the surface of a substrate, as illustrated in FIG. 8. The substrate 40 shown in FIG. 8 has a surface 41 which has depressions (e.g., grooves) formed therein as described above for the apparatus 20. The entire surface 41 or a region of it has a blocking layer that prevents non-specific binding of pathogens to the surface. Multiple separated detection regions 43 are formed on the surface 41 which each have a different binding agent on the surface that is specific to a particular pathogen (e.g., a specific IgG that binds to a particular virus or strain of virus). When a sample is placed in contact with the surface 41, the pathogens present in the sample will be bound in the regions 43 which have the binding agent for that pathogen. The substrate is then rinsed and a liquid crystal material is applied to the surface 41. If any pathogens have been found in a particular region 43, the liquid crystal will appear non-uniform in that region, signaling to the observer the presence in the sample of the pathogen to which that region was specific, allowing an assay for the presence of many pathogens simultaneously in a sample.

As described above, the detection apparatus of the invention may also be incorporated into a "microarray" containing detection regions with different binding agents. Detection apparatus may also be constructed that include detection regions with different sensitivities towards the same pathogen. Such detection apparatus include at least a second detection region on the surface of the substrate. The second detection region has grooves with a width that is different from that in a first detection region; grooves with a depth that differs from those in the first detection region; or grooves with both a width and depth that differs from those in the first detection region. The difference in the dimensions of the grooves of different detection regions allows the microarray to be used where the suspected concentration of the target species is not well known because the concentration of pathogen which results in the disordering of the liquid crystals will differ depending on the width and depth of the grooves in the detection region.

EXAMPLES

Materials

Glass microscope slides used were Fisher's Finest, Premium Grade and were obtained from Fisher Scientific (Pittsburgh, Pa.). Tridecafluoro-1,1,2,2-tetrahydrooctyl trichlorosilane was purchased from Gelest (Tullytown, Pa.). 1-Decanethiol, 1-hexadecanethiol, and mineral oil were obtained from Aldrich (Milwaukee, Wis.). The following were used as thermally- or UV-curable prepolymers: poly (dimethylsiloxane) (PDMS, Sylgard® 184, Dow Corning Co. (Midland, Mich.)); epoxy resin (2-Ton® Clear Epoxy, Devcon (Danvers, Mass.)); polyurethane (PU, NOA61, Norland Products Inc. (New Brunswick, N.J.)); polycyanoacrylate (PC, J-91, Summers Optical (Fort Washington, Pa.)); and polystyrene (PS, UV-74, Summers Optical (Fort Washington, Pa.)). Bovine serum albumin (BSA, IgG free, lyophilized powder) was obtained from Sigma (St. Louis, Mo.) and used as received. The nematic liquid crystal of 4-cyano-4'-pentylbiphenyl (5CB), manufactured by BDH, was purchased from EM industries (Hawthorne, N.Y.).

Silicon Master with Nano-Pattern

As master substrates for replica molding, a patterned silicon wafer (200 nm pattern and 50 nm depth) was prepared by e-beam writing and etching. Before molding the PDMS prepolymer, the original silicon master was silanized by exposing it to fluorinated silane vapor to prevent the PDMS from sticking to the surface of the silicon master. This was accomplished under nitrogen using a glove box (model CC-40, Vacuum Atmospheres Co. (Hawthorne, Calif.)). First, the clean silicon master was attached to a support in a dessicator and suspended face down approximately 2 cm above a 3% (v/v) solution of fluorinated silane (tridecafluoro-1,1,2,2-tetrahydrooctyl trichlorosilane) in heavy mineral oil. Using a vacuum pump, the inner pressure of the dessicator was then adjusted to a pressure of ~0.1 Torr. After ~6 hrs, the dessicator was filled with nitrogen, and the sample was removed. The presence of the fluorinated SAM was confirmed by measurement of the contact angle of water on a reference silicon wafer. The contact angle was measured using a Ramé-Hart model 100 (Mountain Lakes, N.J.) contact angle goniometer. The measured contact angle of water on the fluorinated silicon wafer was over 110°.

Preparation of PDMS Master

Figure 9:
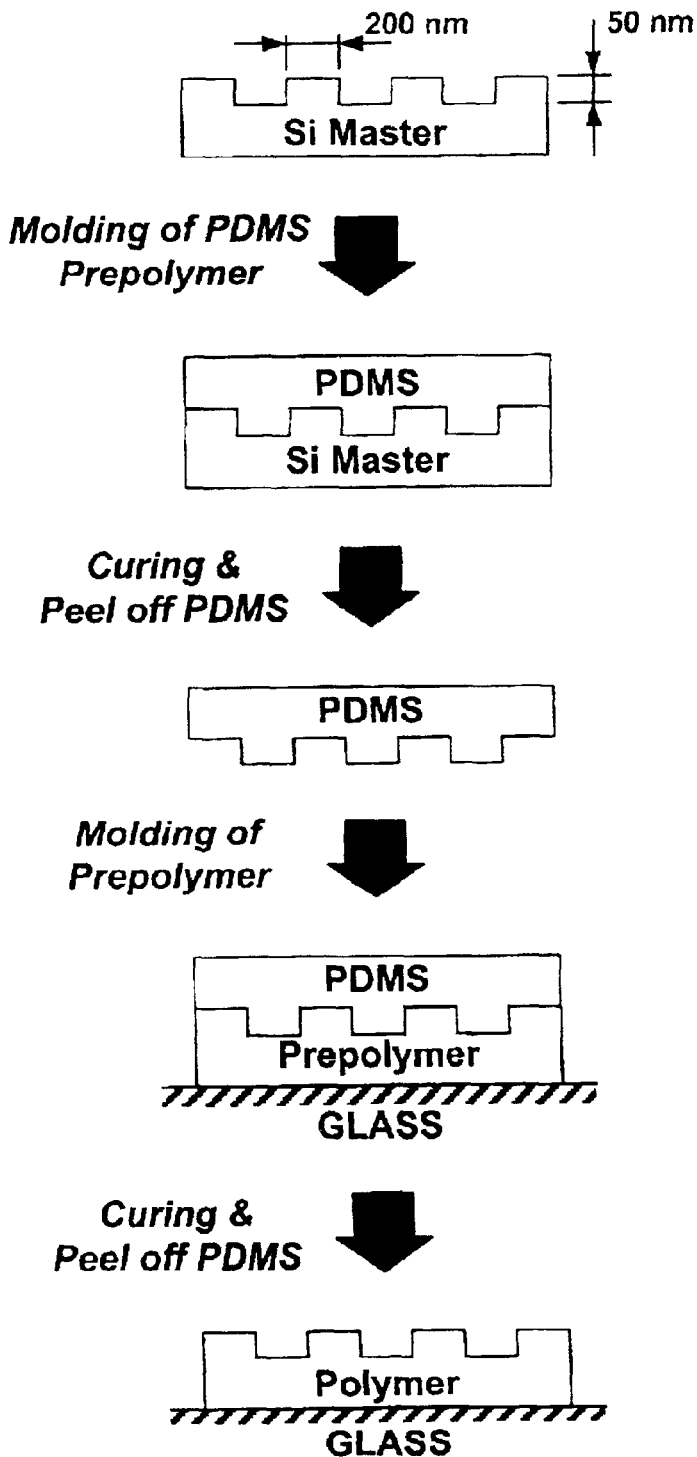
FIG. 9 is a schematic illustration showing the method of forming a polymeric substrate for use in a detection apparatus using a silicon master to form a PDMS master that is subsequently used to form the polymeric substrate.

FIG. 9 schematically illustrates the procedure used for forming a PDMS master from a silicon master prepared as described above. FIG. 9 also illustrates how the PDMS master was used to form substrates from various polymers. Elastomers were used in the formation of masters from the silicon master because they can make conformal contact with surfaces over relatively large areas and because they can be released easily from rigid masters (low interfacial free energy of ~21.6 dyne/cm). Additionally, elastomers typically exhibit good chemical stability. Elastomeric PDMS replicas were fabricated by pouring a mixture of a liquid prepolymer of PDMS and a curing agent (10:1 by weight) over the patterned and fluorinated surface of the silicon master placed in plastic petri dish. To remove entrained air bubbles in the PDMS prepolymer/curing agent mixture that resulted from the mixing and pouring procedure, the petri dish was placed in a vacuum oven for approximately 30 minutes at room temperature. The prepolymer mixture was then cured at 60° C. in a vacuum oven for 1 day. After curing, the PDMS replica was gently peeled away from the silicon master. Finally, the cured PDMS replica was rinsed with ethanol and dried under a gaseous stream of nitrogen.

Polymeric Replicas from Elastomeric PDMS Master

Replication using elastomeric masters has been found to increase the ease of separating the master and the replica, to protect the structures during separation, and to minimize damage to the master that may occur during the replication process. Various polymeric replicas were formed on a glass substrate as schematically illustrated in FIG. 9 using a PDMS master prepared as described above. To form such polymeric replicas from thermally-curing polymers such as epoxy prepolymers, the PDMS replica was placed over a viscous liquid prepolymer of epoxy spread on a glass substrate. The glass substrate was placed on a hot plate and heated to 60° C., and the PDMS replica was pressed into the viscous epoxy prepolymer by applying pressure (~100 g/cm$^2$) for 2 hours. The resulting combination of PDMS and epoxy was then slowly cooled to room temperature before the PDMS replica was peeled from the epoxy substrate. A different process was used to prepare replicas from UV-curable prepolymers such as used to prepared polyurethane, polycyanoacrylate, and polystyrene. To prepare replicas with such UV-curable prepolymers, a PDMS master was first placed on a glass substrate, and ~100 µm thick spacer films (DuPont Films, Wilmington, Del.) were used to maintain a gap between the glass substrate and the PDMS master. Using a syringe, the liquid UV-curable prepolymer was injected between the PDMS master and the glass substrate which was then filled by capillary force on the hot plate (~60° C.). These prepolymers were cured with UV light (365 nm, UV crosslinker, Spectronics Co., Westbury, N.Y.) for 2 hours under nitrogen flow and aged overnight at 60° C. in an oven. After peeling the PDMS master off the surface of the replica, the PDMS master was cleaned with ethanol. A different PDMS master was used for each polymeric material, and it was found that a single PDMS master could be used to fabricate more than 10 polymeric replicas without any noticeable change in the replicated polymeric pattern as confirmed by atomic force microscopy (AFM), optical microscopy, and alignment of liquid crystals.

Incubation of Polymeric Replicas in Aqueous Solution

The polymeric replicas were incubated in phosphate buffered saline (PBS: 137 mM NaCl, 2.7 mM KCl, 4.3 mM $Na_2HPO_4 \cdot H_2O$, 1.4 mM $KH_2PO_4$) or in 1 mg/ml BSA solutions of PBS. After incubation in the aqueous solution, the polymeric replicas were washed gently with deionized water and dried with nitrogen flow before analysis.

Images of Patterned Substrates by AFM

Images of the silicon master, the PDMS masters, and the polymeric replicas were obtained by atomic force microscopy (AFM) using a digital Instruments Nanoscope III (Santa Barbara, Calif.) operating in contact mode or tapping mode. Samples were imaged under ambient conditions using a cantilever made from silicon nitride (spring constant: 0.06 N/m) at a scan rate of 1.0 Hz with 512 sample points per line.

Substrates for Homeotropic Anchoring of Liquid Crystals

Semitransparent and uniformly deposited films of gold with a thickness of ~20 nm were formed on clean glass substrates using an electron beam evaporator (VES-3000-C, Tek-Vac Industries Inc. (Long Island, N.Y.)). The glass slides were mounted on the planetary substrate holder which rotated the slides in an epicyclic manner with respect to the gold source in order to obtain uniform deposition of gold films without a preferred direction. An ~8 nm layer of titanium was used to promote adhesion between the glass and the gold film. The rate of deposition of titanium and gold was ~0.02 nm/sec and the pressure was less than $1 \times 10^{-6}$ Torr before and during evaporation. Mixed self-assembled monolayers (SAMs) were formed on the gold upon immersion in an ethanolic solution containing 85% 1-decanethiol and 15% 1-hexadecanethiol (total concentration of ~1 mM) for 2 hours.

Optical Cells

The alignment of nematic liquid crystal (5CB) on the surfaces of the pattern-transferred polymeric replicas was observed by assembling the films into optical cells. Optical cells were fabricated by pairing two glass slides, in which one side was a polymeric replica fabricated on the glass slide and the other side was a mixed SAM formed on a gold-coated glass slide. Both of these were prepared as described above. The two substrates were kept apart by inserting a thin polyester film (~10 µm thickness of Mylar® brand film (DuPont Films, Wilmington, Del.)) between the surfaces of the substrates. The cells were held together with "bulldog" clips placed along the edge of the glass microscopic slides. The cells were then heated to ~40° C. by placing them on a hot plate. A hot air gun was used to warm the air around the cells to ~40° C. The 5CB was heated into its isotropic phase (~35° C.) within a glass syringe. Then, a drop of 5CB was placed onto the edge of each cell on the hot plate. The 5CB was drawn into the cavity between the two substrates by capillary force. Once filled with 5CB, the cell was removed from the hot plate and cooled in air to room temperature. Upon cooling, the isotropic phase of 5CB transformed to the nematic state.

Analysis of Optical Textures

A polarized light microscope (BX60, Olympus (Tokyo, Japan)) was used to observe the polymeric replica and the optical texture formed by light transmitted through the optical cells filled with nematic 5CB. Images of the optical appearance of the liquid crystal cells were captured with a digital camera (C-2020 Z, Olympus America Inc. (Melville, N.Y.)) that was attached to the polarized light microscope. The pictures were obtained using high quality mode (resolution of 1600×1200 pixels) at an aperture of f11 and a shutter speed of ⅙ sec for the observation of the polymeric replica (microscope setting: light source of 100% of maximum intensity and 100% open aperture) whereas a shutter speed of 1/320 sec was used for observing the optical cells prepared from the polymeric replicas (microscope setting: light source of 50% of maximum intensity and 50% open aperture).

Coating of Polymeric Replicas with Gold

Semitransparent films of gold with a thickness of ~10 nm were deposited onto molded polyurethane substrates using an electron beam evaporator (VES-3000-C, Tek-Vac Industries Inc. (Long Island, N.Y.)). The substrates were mounted on the planetary substrate holder which rotated the slides in an epicyclic manner with respect to the gold source in order to obtain uniform deposition of gold films without a preferred direction. An ~3 nm layer of titanium was used to promote adhesion between the polyurethane and the gold film. The rate of deposition of titanium and gold was ~0.02 nm/sec and the pressure was less than $1 \times 10^{-6}$ Torr before and during evaporation.

Chemical Patterning of Gold Coated Polymeric Replicas

A flat piece of PDMS (approximately 1 cm×1 cm×1 cm) was "inked" with a 3 mM ethanolic solution of hexadecanethiol. The excess ink was removed from the surface of the PDMS stamp and then the stamp was placed under a stream of flowing nitrogen for 3 minutes. The stamp was then contacted with the surface of the gold coated polyurethane substrate without application of additional pressure. Contact was maintained between the gold-coated substrate and the stamp for approximately 10 seconds. This procedure lead to the formation of a self-assembled monolayer of hexadecanethiol on the top surfaces of the topography on the surface. The sides and bottom of the topography on the substrate was "bare gold". The whole substrate was then immersed into a 0.1 mM ethanolic solution of $HS(CH_2)_{11}(OCH_2CH_2)_2OH$ for 30 seconds. This procedure lead to the formation of a SAM on the sides and bottom of the topography, but not the top because it was already functionalized with a SAM formed from hexadecanethiol.

Binding of Magnetic Beads to Biotinylated BSA-Coated Replicas

Optical diffraction gratings were purchased from ES Edmund Industrial Optics (Barrington, N.J.) with the characteristics shown in Table 1.

TABLE 1

Properties of Optical Diffraction Gratings

| Sample Number | Grooves/mm | Blaze Angle | Stock Number |
|---|---|---|---|
| 1 | 300 | 2°34' | J43-737 |
| 2 | 600 | 5°09' | J43-741 |
| 3 | 600 | 8°37' | J43-742 |
| 4 | 600 | 13°00' | J41-020 |
| 5 | 600 | 17°27' | J43-748 |
| 6 | 600 | 28°41' | J43 749 |
| 7 | 1200 | 36°52' | J43-754 |
| 8 | 3600 | — | J43-227 |

Before molding the PDMS prepolymer, the diffraction grating was silanized by exposing it to fluorinated silane vapor to prevent the PDMS from sticking to the surface of it. This was accomplished under nitrogen using a glove box (model CC-40, Vacuum Atmospheres Co. (Hawthorne, Calif.)). First, the grating was attached to a support in a dessicator and suspended face down approximately 2 cm above a 3% (v/v) solution of fluorinated silane (tridecafluoro-1,1,2,2-tetrahydrooctyl trichlorosilane) in heavy mineral oil. Using a vacuum pump, the inner pressure of the dessicator was then adjusted to a pressure of ~0.1 Torr. After ~6 hours, the dessicator was filled with nitrogen, and the sample was removed.

After mixing the PDMS prepolymer with the curing agent (in a 1/10 proportion), the mixture was placed for 30 minutes in a vacuum oven at 60° C. to remove dissolved gasses. The polymer was poured onto the diffraction grating, placed in the vacuum oven for 5 minutes and then placed on hot plate at 60° C. overnight.

Epoxide replicas were prepared from the PDMS masters by placing epoxy resin an OTS-treated glass slide and then pushing the PDMS master into it. The epoxide was cured by placing it on a hot plate for 30 minutes. The epoxy replicas were treated with the biotin-BSA solution (2 mg/mL in PBS) for 2 hours. This short immersion time was found not to destroy the topography of the micrometer-epoxy replicas. Longer immersion times did cause obvious damage. 20 μL of aqueous solution containing $6.7 \times 10^9$, $6.7 \times 10^8$, $6.7 \times 10^7$, $6.7 \times 10^6$ and $6.7 \times 10^5$ magnetic beads per milliliter of PBS was placed on top of the BSA-treated or biotin-BSA treated epoxy replicas. A magnet was placed under the surface to draw the beads to the surface of the replicas.

The liquid crystal cells were constructed using the microscope slides treated with OTS and the epoxy replica treated with the biotin-BSA solution with and without magnetic beads. The liquid crystal was placed between the epoxy surface and the OTS treated glass slide using spacers of 12 to 15 μm. The optical appearance of the cells was determined using a polarized microscope.

Results and Discussion

Pattern Transfer by Replica Molding

Figure 10:
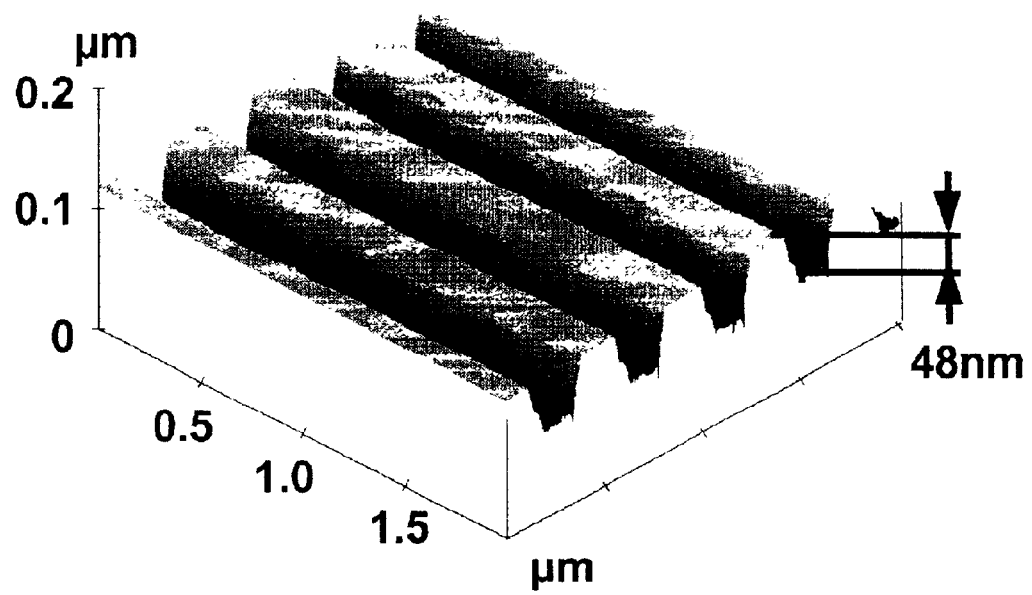
FIG. 10 is a three-dimensional plot of an AFM image of a silicon master used to form a PDMS replica.
Figure 11:
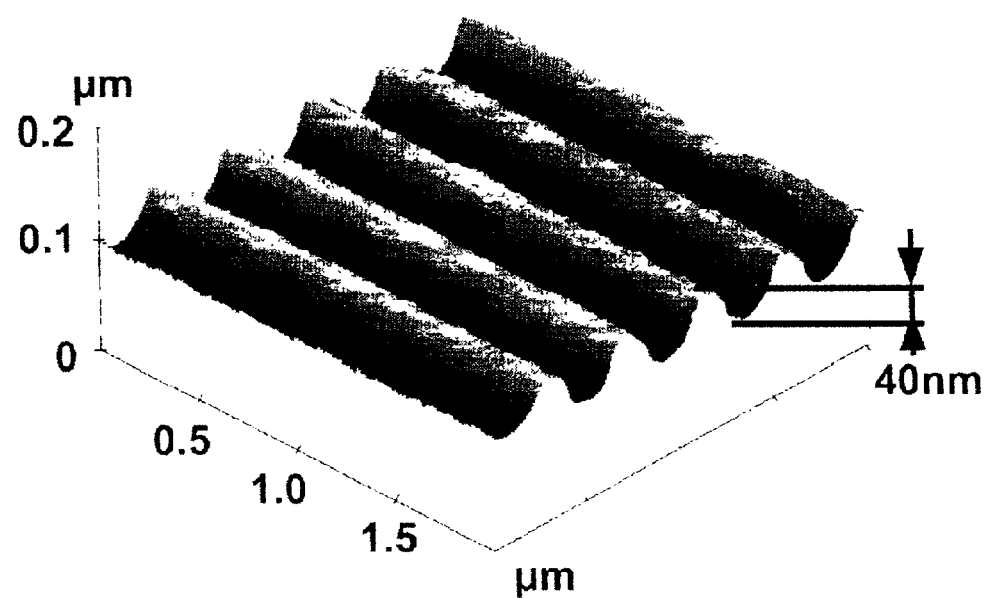
FIG. 11 is a three-dimensional plot of an AFM image of a PDMS replica formed from a silicon master.
Figure 12:
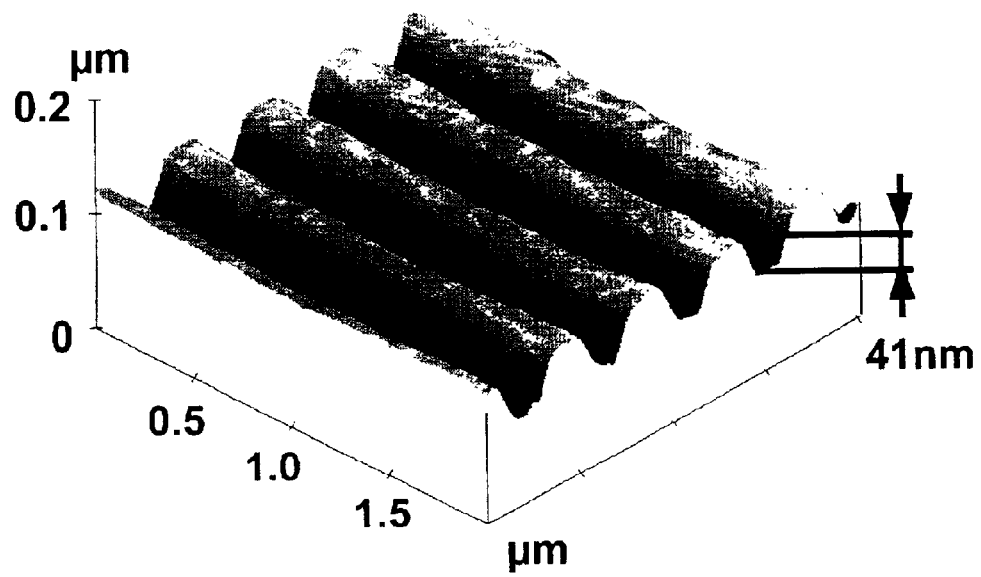
FIG. 12 is a three-dimensional plot of an AFM image of an epoxide replica formed from a PDMS replica before the epoxide replica is immersed in aqueous solution.

An SEM image of the fluorinated silicon master was obtained to determine its topographical features. The cross-sectional SEM image indicated a well-defined topography that included periodic structures with a depth of ~49 nm and a width of ~200 nm. AFM images of the silicon master, the PDMS replica prepared from the silicon master, and the polymeric replicas prepared from the PDMS replica were obtained for comparison. The structure and shape of the AFM image of the silicon master is shown in FIG. 10, and it is consistent with the SEM image obtained. The consistency of the AFM and SEM images of the silicon master indicates that AFM images obtained in contact mode give reliable results and may be used to analyze the topography of the replicated polymeric substrates. The decreased quality in the topography shown in the AFM image of the PDMS master (FIG. 11) is a characteristic of the AFM image of the elastomeric materials. Thus, the imperfections of topography shown in the AFM image of the PDMS master is probably due to the distortion by the probe rather than to any real imperfection in the surface. The most important feature of replication is the nanometer-scale structure in polymeric substrates replicated from the PDMS master. Because the polymeric materials used in this study form rigid films after curing, AFM images of these replicas (FIGS. 12–15, respectively the AFM images of the replicas formed from epoxy, polyurethane, polycyanoacrylate, and polystyrene) formed from the PDMS master do not show the variability in topography shown by the flexible PDMS replica (FIG. 11). Surprisingly and unexpectedly, FIGS. 12–15 demonstrate that the depth and width of the pattern in the silicon master is faithfully reproduced in each of the polymeric replicas despite the poor AFM image of the PDMS master. The slight decrease in the depth of the pattern shown in the polymeric replicas is explained by the stepwise replication procedure in forming the polymeric replicas from the silicon master.

The AFM images of the polymeric substrates show the different qualities in the shape of the transferred patterns (such as depth and sharpness of the patterned edge). Replication was repeated at least three times for each polymeric material. Observation of the AFM images showed that the polyurethane replicas had the best overall pattern quality in the transfer of the pattern from the silicon master. Because the hardnesses of the polymeric replica materials after curing is almost the same (83~90 Shore D hardness), the difference in pattern quality is not a result of differing hardness which was the case for the PDMS replica (~50 Shore A hardness). Shrinkage during curing of the prepolymers also does not seem to be an important factor influencing the quality of replicated patterns. Although FIGS. 12–15 show that different polymeric materials will produce varying results in replicas formed therefrom, FIGS. 12–15 show that each of the materials used formed replicas suitable enough for further investigation.

AFM Images of Polymeric Replicas after Incubation in Aqueous Solution

Figure 16:
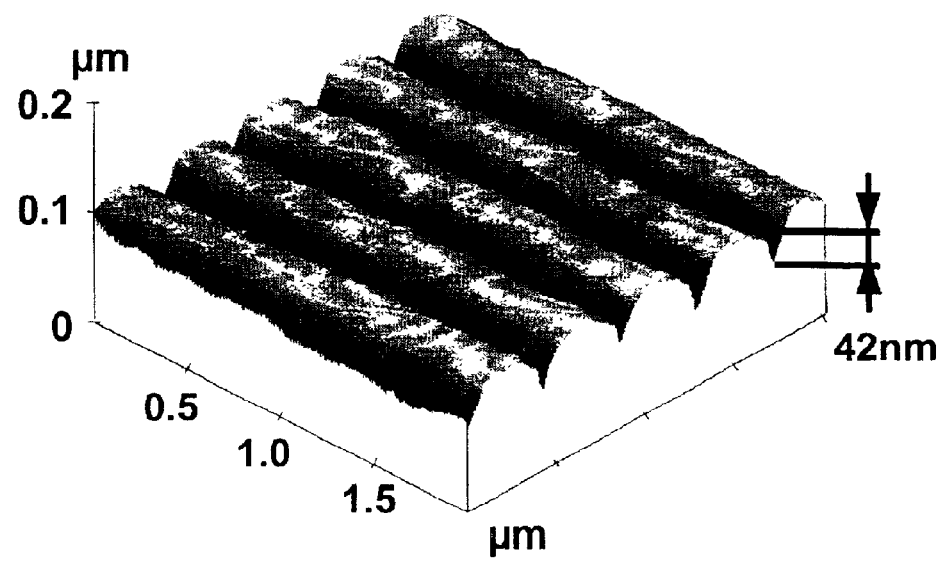
FIG. 16 is a three-dimensional plot of an AFM image of an epoxide replica formed from a PDMS replica after the epoxide replica was immersed in an aqueous PBS solution for one hour.

The polymeric replicas were incubated in aqueous solutions to analyze their ability to withstand exposure to test solutions containing possible target species. Specifically, the polymeric substrates were incubated in PBS solution for 1 day. Then, the structure and shape of the resulting pattern was observed using AFM (FIGS. 16–19). The pattern of the epoxy replica did not survive immersion in the aqueous solution. After one day in the aqueous solution, most of the epoxy-pattern formed on the glass disrupted and detached from the glass. FIG. 16 shows the AFM image of the epoxy replica after incubation for 1 hour in PBS. Swelling of the pattern in the epoxy replica is apparent in the AFM image.

Figure 13:
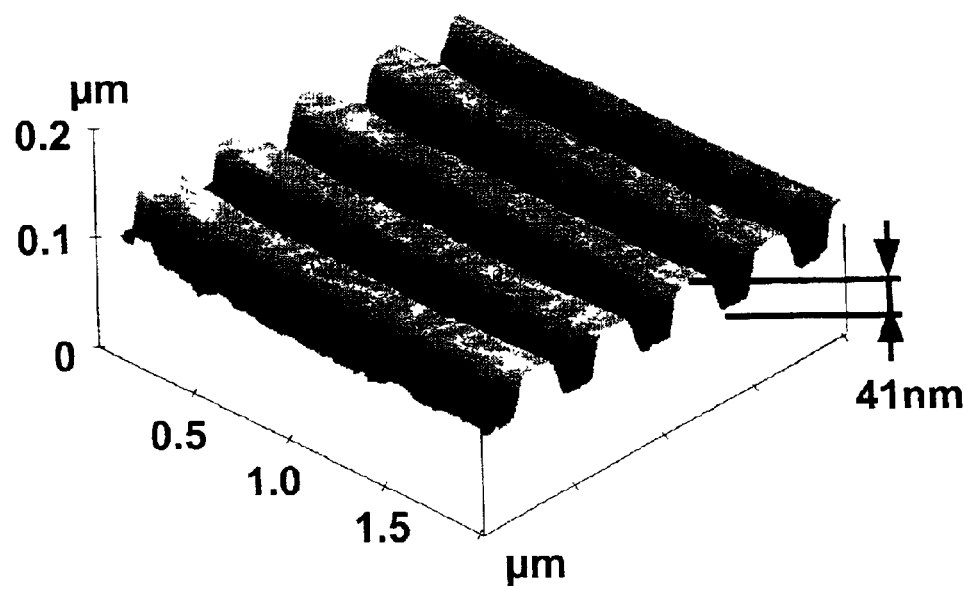
FIG. 13 is a three-dimensional plot of an AFM image of a polyurethane replica formed from a PDMS replica before the polyurethane replica is immersed in aqueous solution.
Figure 14:
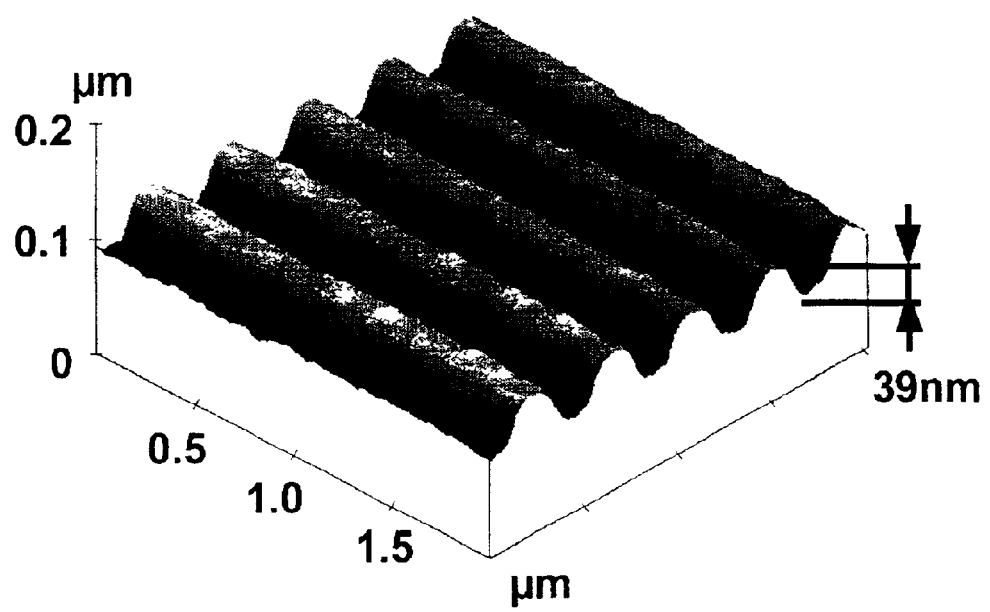
FIG. 14 is a three-dimensional plot of an AFM image of a polycyanoacrylate replica formed from a PDMS replica before the polycyanoacrylate replica is immersed in aqueous solution.
Figure 15:
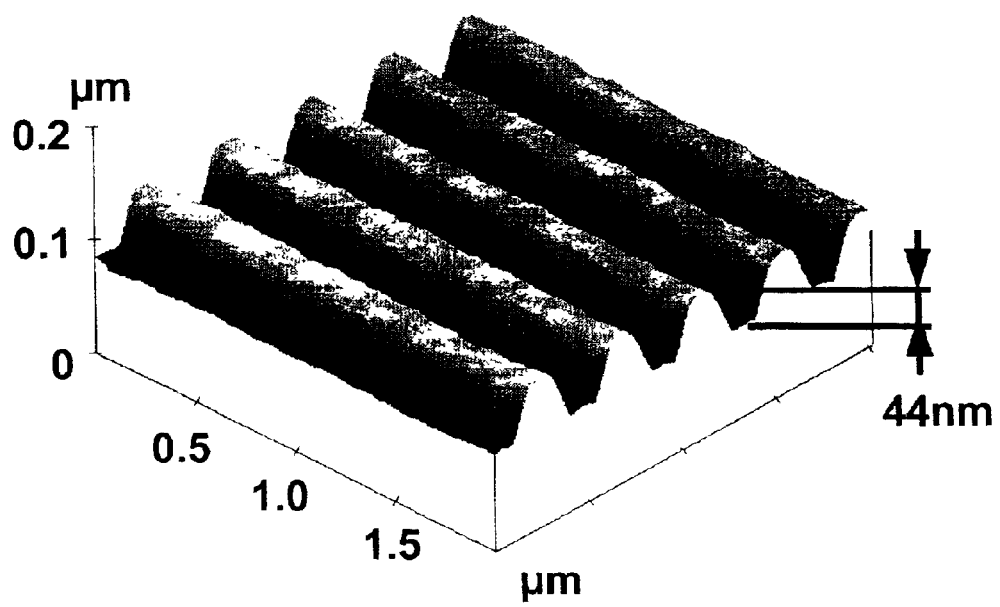
FIG. 15 is a three-dimensional plot of an AFM image of a polystyrene replica formed from a PDMS replica before the polystyrene replica is immersed in aqueous solution.
Figure 17:
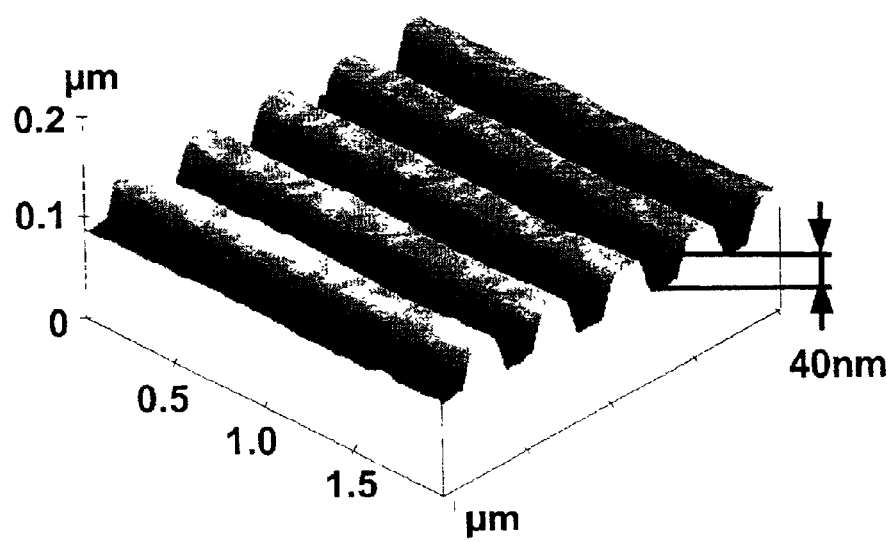
FIG. 17 is a three-dimensional plot of an AFM image of a polyurethane replica formed from a PDMS replica after the polyurethane replica was immersed in an aqueous PBS solution for one day.
Figure 18:
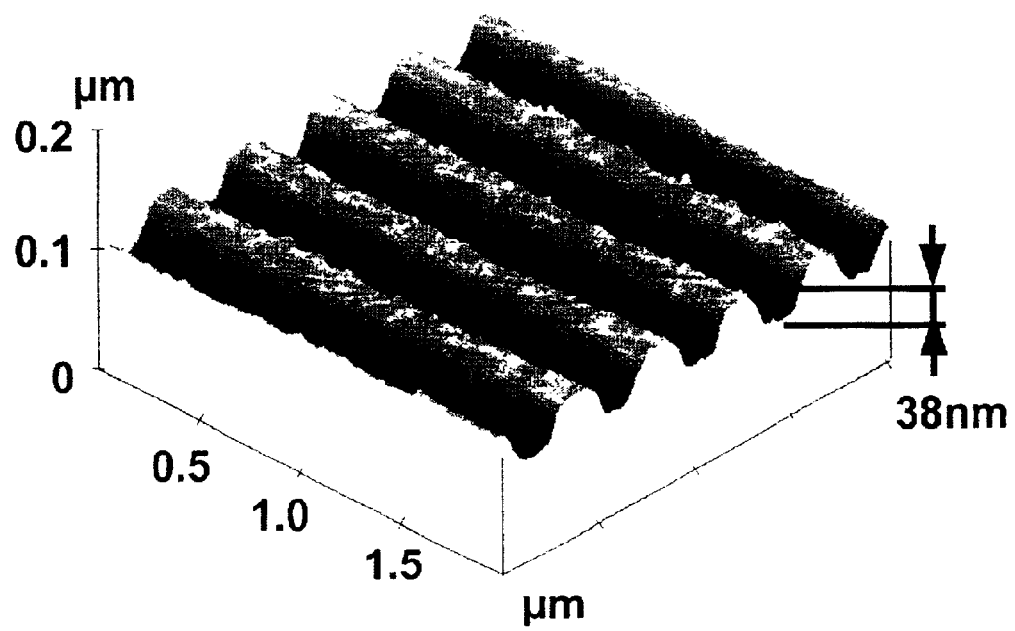
FIG. 18 is a three-dimensional plot of an AFM image of a polycyanoacrylate replica formed from a PDMS replica after the polycyanoacrylate replica was immersed in an aqueous PBS solution for one day.
Figure 19:
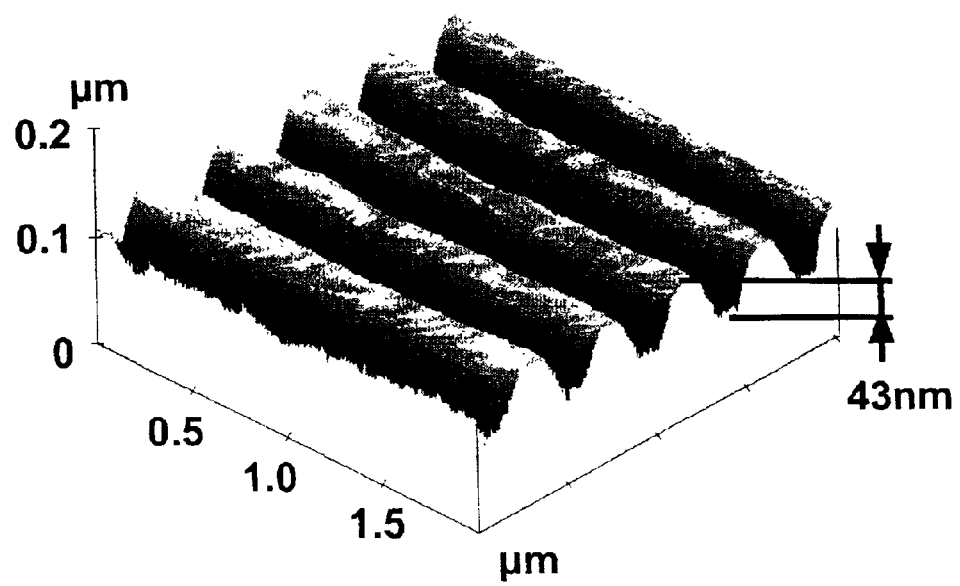
FIG. 19 is a three-dimensional plot of an AFM image of a polystyrene replica formed from a PDMS replica after the polystyrene replica was immersed in an aqueous PBS solution for one day.

In contrast to the epoxy replica, the AFM images of replicas prepared from polyurethane, polycyanoacrylate, and polystyrene did not show distinguishable changes in the pattern after incubation in PBS for 1 day. That is, the AFM images of PU, PC and PS replicas after incubation in PBS, respectively shown in FIGS. 17–19, are almost the same as images of the patterns before incubation (FIGS. 13–15). However, the PC and PS replicas were noticeably hazy after incubation in PBS for 1 day. This was considered to be caused by swelling. The hazy features in these replicas disappeared after drying with nitrogen. As respectively shown in FIGS. 18 and 19, the swelling in the PC and PS replicas did not cause any noticeable change in the AFM images of the pattern in the polymeric replicas. Even though the appearance of swelling indicates that prolonged incubation of polymeric substrates in aqueous solutions may damage the pattern of polymeric replicas, the fact that the structure was unaffected demonstrates that these polymers are suitable for use as substrates in the present invention. The swelled feature found in the epoxy replica did not recover after drying. No haziness was observed in the replica prepared from polyurethane after incubation in PBS for 1 day, and FIGS. 13 and 17 demonstrates that the shape and structure of the polymeric pattern were not changed upon incubation in PBS.

Optical Images of the Polymeric Replicas between Crossed Polarizers

The polymeric replicas formed on glass substrates are optically transparent. Thus, optical microscopy could be used to analyze the impact of incubation in aqueous media on the patterns of the various replicas. The results indicated that the epoxy replica was severely and irreversibly damaged by incubation in PBS for 1 hour. The PC and PS replicas were also found to exhibit some swelled and damaged features. Even after the haziness disappeared in these substrates, scars of swelling damage to the patterned substrates remained. Although incubation in dried air for long periods was found to reduce the intensity and population of scars, it was apparent that the PC and PS replicas were also damaged by incubation in the aqueous media. In contrast, these experiments demonstrated that the polymeric replica of PU was not damaged by incubation in PBS. Therefore, the analysis using AFM and optical microscopy indicated that polyurethane is an especially preferred polymer for use in replication and biological applications according to the present invention.

Alignment of Liquid Crystals on the Surface of Patterned Polymeric Replicas

Because the grooved structures in substrates can uniformly align liquid crystals in the direction of the grooves, liquid crystals may be used to investigate the alignment properties of the patterned surfaces. Thus, optical cells based on liquid crystals were used to investigate the polymeric replicas. First, reference substrates were prepared that show homeotropic anchoring of liquid crystals (5CB). The homeotropic anchoring of 5CB does not change the polarization of light passed through the optical cell. Thus, the optical textures representing the anchoring of 5CB on the patterned surfaces of the replicas could be observed using the reference substrate as one substrate in the optical cell and the polymeric replica as the other substrate. The substrate exhibiting homeotropic anchoring of 5CB was obtained as described above using mixed self-assembled monolayers (SAMs) formed by coadsorption of long and short alkanethiols on uniformly deposited gold substrates. An optical cell prepared from two substrates with mixed SAMs on the gold substrates indicated homeotropic anchoring of 5CB i.e. its optical appearance was dark regardless of whether the optical cell was rotated. The homeotropic anchoring of the liquid crystal in this optical cell was also supported by conoscopic interference.

Optical cells were next prepared by replacing one substrate of the optical cell with the two substrates prepared from alkanethiols and gold with a patterned substrate or with a non-patterned substrate. The optical textures resulting from anchoring of 5CB on the patterned surfaces of the replicas could thus be observed and recorded. Glass slides were used as a non-patterned substrate, and rubbed glass slides were initially used as a patterned substrate. 5CB is non-uniformly anchored on a clean glass substrate, but simple rubbing of glass slides with a cloth results in uniform alignment of 5CB in the rubbing direction (direction of pattern). The optical textures obtained from the optical cell prepared using a rubbed glass slide showed strong modulation between dark and light upon rotating the optical cell. This result demonstrates uniform alignment of 5CB in the direction of the rubbing. In contrast, when the non-patterned substrate was used as one of the substrates in the optical cell, the optical appearance showed non-uniform orientation of 5CB as evidenced by the lack of modulation in the light transmitted as a function of rotation of the optical cell between crossed polarizers. Therefore, the use of a reference substrate showing homeotropic anchoring of 5CB in an optical cell may be used to visualize and amplify the alignment of liquid crystals on the patterned polymeric substrates.

Optical cells were next prepared using one reference substrate that homeotropically anchored 5CB and a second substrate which was one of the polymeric replicas. For all polymeric substrates, the anchoring of 5CB in the patterned area could be differentiated from that in the non-patterned area. The patterned area of the polymeric replicas produced dark images when the direction of the pattern was parallel to the polarizers. Additionally, rotating the optical cell between crossed polarizers produced strong modulation between dark and light. In contrast, the optical textures in the non-patterned area of the replicas showed little optical modulation upon rotation of the optical cells.

Although the overall features in the optical textures of all the optical cells prepared using the polymeric replicas indicated anchoring of 5CB toward the patterned direction, the quality of uniform alignment of 5CB on the polymeric replicas differed depending upon the polymeric material used. At least three optical cells were prepared using different replicas for each polymeric material. The optical features of these cells were quite reproducible for each polymeric material. For example, the epoxy and PS replicas showed clear and uniform alignment of 5CB (uniform and featureless) over the entire range of the patterned area. On the other hand, optical cells prepared from the PU replica induced poor alignment of 5CB toward the patterned direction (flow patterns observed in the optical texture of these cells indicate the coexistence of slightly different orientations of 5CB).

Alignment of Liquid Crystals on the Polymeric Replicas After Incubation in Aqueous Media The optical appearance of liquid crystals anchored on the surfaces of the polymeric replicas after incubation in PBS was examined. Disruption in the uniform alignment of 5CB was observed in the epoxy replica after it had been incubated in PBS for 1 hr as compared with the alignment of 5CB before incubation. The optical texture of 5CB anchored on the surface of the PU replica did not show complete uniform orientation as many flow patterns were observed in the texture. However, incubation in PBS for 1 day did not produce any noticeable changes in the optical texture of the PU replica.

The optical texture from the anchoring of 5CB on the PC replica exhibited a significant number of disclination loops indicating the existence of domains having slightly different orientations of liquid crystal. The reduction in the uniformity of the optical texture of the liquid crystal on the PC replica was observed both before and after immersion in the PBS, and no extensive differences were observed between the optical textures obtained before and after exposure to the aqueous media. As discussed above, incubation in PBS for 1 day damaged the surfaces of the PC and PS replicas as confirmed by microscopy. Although, the non-uniform features found in the optical cells prepared from the PC replicas might be explained by the damage to the surface, this does not explain the optical texture of the optical cell prepared from the PS replica which showed perfect alignment of 5CB which was not changed by incubation in PBS. Thus, although both the PC and PS replicas appeared hazy after incubation in aqueous media, the difference in the optical textures of 5CB after incubation of the replicas in PBS is consistent with the results obtained using optical microscopy. It was thus concluded that the PC replica was much more severely damaged by immersion in the aqueous media than was the PS replica. Although incubation of PS replicas in aqueous media for extended periods might damage the patterned surface, the PS replica is a very useful substrate for application in the present invention.

Alignment of Liquid Crystals on the BSA-coated Polymeric Replica Surface

As noted above, the PU replica showed excellent properties with respect to replication and stability in aqueous solution. However, the optical textures of 5CB anchored on the patterned surface of the PU replica showed non-uniform features of 5CB such as flow patterns. Because the liquid crystal is a small molecule and amplifies the surface properties based on its anchoring on the surface, it provides information about surface features that was not detected using AFM or optical microscopy.

Based on the assumption that the surface of the PU replica has structures that result in non-uniform liquid crystal alignment, new approaches were used to induce the uniform alignment of 5CB on PU replicas. Thus, the physical adsorption of small biomolecules on the surface of polymeric replicas was investigated to determine whether these could be used to alter surface properties and improve performance without erasing the morphology of patterned surfaces of ~200 nm width and ~50 nm depth. Thus, the polymeric replicas prepared as described above were incubated in PBS solutions containing bovine serum albumin (BSA) because BSA easily adsorbs on most surfaces and its size is such that it should not disturb the patterns on the polymeric replicas. In addition, BSA films induce planar anchoring of 5CB on substrate surfaces prepared from PDMS. It was hypothesized that if the adsorbed BSA layer covers the surface of polymeric replicas enough to erase the flow patterns that were exhibited in the PU replicas, then uniform alignment of 5CB would result and PU would be an excellent material for use as a substrate in the present invention. However, the optical appearance of 5CB in the PU replica was almost the same as that observed before exposure to BSA. Thus, the adsorbed BSA layer does not act as an effective layer for erasing the flow patterns in the PU replica. In direct contrast, the uniform alignment of 5CB observed in the PS replica incubated in a PBS solution containing BSA demonstrates that coating this polymeric substrate with small molecules is a simple yet effective method for changing the surface properties without losing the morphology of the patterned surface.

Polymeric replicas of polyurethane and polystyrene were coated with gold using the procedures described above. When SAMs formed from alkanethiols were formed on the surfaces of these substrates, we observed that liquid crystals placed into contact with them were uniformly anchored along the direction of the grooves. Whereas polyurethane replicas and BSA-coated polyurethane replicas did not provide highly uniform alignment of the liquid crystal, the gold coating does lead to uniform alignment of the liquid crystal on the PU substrates.

SAMs were patterned on the gold coated polyurethane substrates using the procedures described above. Whereas hexadecane did not spread across a gold-coated polyurethane substrate that had been functionalized with a SAM formed from hexadecanethiol, the existence of the pattern was confirmed by observing the spreading of a droplet of hexadecane across the surface patterned with hexadecanethiol and $HS(CH_2)_{11}(OCH_2CH_2)_2OH$.

Detection was accomplished using the 2.8 micrometer magnetic beads coated with streptavidin using polymer substrates molded from optical diffraction gratings. The polymer replicas were coated with biotinylated BSA using the procedures described above. The beads suspended in PBS were dispensed onto the surface of the biotinylated-BSA-coated substrate. A magnet was then placed under the substrate to draw the beads towards the coated surface of the substrate. After 5 minutes, the magnet was removed and the surface was rinsed. The presence of the beads on the surface was confirmed by optical microscopy. Whereas liquid crystal was uniformly aligned along the grooves in the absence of bound beads, the presence of the bound beads lead to disruption of the uniform alignment of the liquid crystal.

Patterning of Polymeric Replicas

Gold-coated polyurethane replicas are made hydrophobic by immersing them into ethanolic solutions of hexadecanethiol at a concentration of about 1 mM. A PDMS stamp with a flat surface formed by molding it against a flat polystyrene surface is inked with BSA by immersing it in an aqueous solution of BSA at a concentration of about 10 mg/mL for about 30 minutes. The surface of the stamp is rinsed with PBS and then water before drying it under a stream of gaseous nitrogen. The surface of the stamp is then contacted with the surface of the hydrophobic replica for about 1 second to transfer BSA onto the tops of the ridges of the grooves of the replica. The entire replica is then immersed for 10 minutes in an aqueous solution of anti-VSV-Indiana at a concentration of about 50 µg/mL so that the anti-VSV-Indiana immunoglobulin is adsorbed in the depressions or grooves of the replica. In this manner, substantially all of the binding agent is found in the depressions of the detection region of the replica. Immersing the replica in an aqueous sample containing the Indiana strain of VSV at a concentration of about $10^6$ pfu/mL leads to the binding of the VSV in the grooves of the replica disrupting the anchoring of liquid crystal in the grooves.

It is understood that the invention is not limited to the embodiments described above for illustration, but embraces all such forms thereof as come within the scope of the following claims.

What is claimed is:

1. A method for use in detecting the presence of a selected microscopic pathogen in a sample comprising:
   (a) providing a substrate having a detection region thereon comprising a surface comprising microstructures including depressions having width and depth, wherein:
      (i) the width and depth of the depressions are selected in size to align a liquid crystal material in contact therewith;

(ii) the width and depth of the depressions are selected in size to be occupied by the selected pathogen; and (iii) the width of the depressions are on the order of the size of the selected pathogen;

(b) treating the surface of the detection region to provide a layer thereon that blocks non-specific binding of pathogens to the surface and that includes a binding agent that specifically binds the selected pathogen to be detected;

(c) applying a sample to be tested for the presence of the specific pathogen to the surface of the detection region of the substrate, wherein when the specific pathogen is present in the sample the specific pathogen binds to the binding agent and at least partially occupies the depression; and (d) thereafter applying the liquid crystal material to the detection region that will be aligned by the microstructures on the surface of the substrate in the absence of binding pathogen particles to the surface of the substrate, wherein the presence of the selected pathogen bound to the binding agent and at least partially occupying the depression will be manifested by a visually observable disordering of the liquid crystal material.

2. The method of claim 1, further comprising coating at least a portion of the detection region with an inorganic material selected from the group consisting of an oxide of silicon, an oxide of a metal, a metal, and combinations thereof.

3. The method of claim 2, wherein the inorganic material is silver or gold and the method further comprises treating at least a portion of the silver or gold with a mercaptan or a disulfide.

4. The method of claim 1, wherein the substrate is formed of a molded polymer plastic.

5. The method of claim 4, wherein the molded polymer plastic comprises polystyrene, polycyanoacrylate, or polyurethane.

6. The method of claim 4, wherein the molded polymer is polydimethylsiloxane.

7. The method of claim 1, wherein the treating of the surface of the detection region includes applying bovine serum albumin to the surface of the detection region of the substrate.

8. The method of claim 7, wherein the treating of the surface of the detection region includes applying an immunoglobulin or a portion thereof to the detection region surface that provides a specific binding site for the selected pathogen.

9. The method of claim 1, wherein the selected pathogen is a virus and the depressions on the surface of the detection region have a width and depth in the range of 5 nm to 500 nm.

10. The method of claim 1, wherein the depressions on the surface of the detection region of the substrate comprise parallel grooves having a width of approximately 100 nm.

11. The method of claim 10, wherein the grooves are separated by ridges having a width of about 100 nm.

12. The method of claim 10, wherein the grooves have a depth of approximately 100 nm.

13. The method of claim 1, wherein the binding agent is selected from the group consisting of peptides, polypeptides, RNA, DNA, biotin, avidin, fragments of antibodies, antibodies, and sugars.

14. The method of claim 1, wherein the selected pathogen is a bacteria and the depressions on the surface of the detection region have a width and depth in the range of 0.1 $\mu$m to 10 $\mu$m.

15. The method of claim 1, wherein substantially all the binding agent is located in the depressions of the detection region.

* * * * *

UNITED STATES PATENT AND TRADEMARK OFFICE
CERTIFICATE OF CORRECTION

PATENT NO. : 6,797,463 B2
DATED : September 28, 2004
INVENTOR(S) : Abbott et al.

It is certified that error appears in the above-identified patent and that said Letters Patent is hereby corrected as shown below:

Column 1,
Lines 12-13, delete "ONR N00014-97-0702" and replace it with -- ONR 00014-97-1-0703 --.

Column 4,
Line 29, delete the phrase "these principles has also been" and replace it with -- these principles have also been --.
Lines 30-31, delete the comma after the word "vesicles," to read -- research based on vesicles reveals ... --.

Column 9,
Lines 29-30, delete the phrase "Polystyrene is an especially preferred substrates" and replace it with -- Polystyrene is an especially preferred substrate --.

Column 14,
Line 54, delete the phrase "such as used to prepared" and replace it with -- such as used to prepare --.

Signed and Sealed this

Twenty-third Day of August, 2005

JON W. DUDAS
*Director of the United States Patent and Trademark Office*